United States Patent  [19]

(12) United States Patent
Berman et al.

(10) Patent No.: US 7,141,036 B2
(45) Date of Patent: *Nov. 28, 2006

(54) METHODS OF APPLYING A MEDICINAL SUBSTANCE

(75) Inventors: Irwin R. Berman, Saint Simons Island, GA (US); Richard D. Gillespie, Athens, TX (US); Gervasio Salgado, Marbella (ES)

(73) Assignee: Syringe, LLC, Saint Simons Island, GA (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/160,166

(22) Filed: Jun. 4, 2002

(65) Prior Publication Data

US 2003/0225358 A1   Dec. 4, 2003

(51) Int. Cl.
*A61M 31/00*   (2006.01)
*A61F 13/20*   (2006.01)
(52) U.S. Cl. .............. 604/60; 604/15; 604/57
(58) Field of Classification Search ........... 604/11–18, 604/47, 36–38, 48, 57–64, 289, 310, 311, 604/290, 193; 222/249, 250, 386, 288, 319
See application file for complete search history.

(56) References Cited

U.S. PATENT DOCUMENTS

| 694,971 | A |   | 3/1902 | Kistler |
|---|---|---|---|---|
| 1,567,009 | A | * | 12/1925 | Sterritt ....................... 604/182 |
| 1,818,670 | A |   | 8/1931 | Bixler |
| 2,474,496 | A |   | 6/1949 | Rayman |
| 2,631,586 | A | * | 3/1953 | Reilly ......................... 604/104 |
| 2,695,023 | A |   | 11/1954 | Brown |
| 2,764,981 | A |   | 10/1956 | Helmer et al. |
| 2,875,761 | A |   | 3/1959 | Helmer et al. |
| 3,076,455 | A |   | 2/1963 | McConnaughey et al. |
| 3,429,642 | A |   | 2/1969 | Underwood |
| 3,894,539 | A |   | 7/1975 | Tallent |
| 3,934,586 | A |   | 1/1976 | Easton et al. |
| 4,017,007 | A |   | 4/1977 | Riccio |
| 4,439,180 | A | * | 3/1984 | Kline .......................... 604/48 |
| 4,466,426 | A |   | 8/1984 | Blackman |

(Continued)

FOREIGN PATENT DOCUMENTS

DE   3513646 A1   10/1986

(Continued)

OTHER PUBLICATIONS

Salgado et.al., "Headaches in the Treatment of Anal Fissures," Diseases of the Colon & Rectum, 1999, vol. 42, No. 8, p. 1106.

(Continued)

*Primary Examiner*—Kevin C. Sirmons
*Assistant Examiner*—Benjamin Huh
(74) *Attorney, Agent, or Firm*—J. Bruce Hoffnagle

(57) ABSTRACT

A method of applying a medicinal substance onto an area within a patient's body cavity includes providing an applicator formed by six integral sections. A proximal section is formed with an entry passage. An axial intermediate passage of the applicator extends from the entry passage through a flange section and a passage section. A slot section has a slot delivery passage communicating with the axial intermediate passage, and at least one axially-elongated slot therethrough. A solid section extends from the slot section, and a dome section extends to an end of the applicator. The method further includes locating the slot delivery passage adjacent the area within the cavity, forming a substance mass externally of the cavity, moving the mass into the slot delivery passage, and moving at least a portion of the substance onto the area.

3 Claims, 19 Drawing Sheets

U.S. PATENT DOCUMENTS

| | | |
|---|---|---|
| 4,560,376 A | 12/1985 | Cannon |
| 4,585,445 A | 4/1986 | Hadtke |
| 4,654,035 A | 3/1987 | Ando |
| 4,659,327 A | 4/1987 | Bennett et al. |
| 4,874,385 A | 10/1989 | Moran et al. |
| 4,997,423 A | 3/1991 | Okuda et al. |
| 5,048,684 A | 9/1991 | Scott |
| 5,217,436 A | 6/1993 | Farkas |
| 5,217,442 A | 6/1993 | Davis |
| 5,219,448 A | 6/1993 | Hackmann |
| 5,279,586 A | 1/1994 | Balkwill |
| 5,431,680 A | 7/1995 | Jones |
| 5,433,352 A | 7/1995 | Ronvig |
| 5,451,214 A | 9/1995 | Hajishoreh |
| 5,478,321 A | 12/1995 | Kimber |
| 5,531,703 A | 7/1996 | Skwarek et al. |
| 5,599,314 A | 2/1997 | Neill |
| 5,609,581 A * | 3/1997 | Fletcher et al. ............. 604/212 |
| 5,688,252 A | 11/1997 | Matsuda et al. |
| 5,695,481 A * | 12/1997 | Heinzelman et al. ....... 604/279 |
| 5,728,076 A | 3/1998 | Loos et al. |
| 5,769,825 A | 6/1998 | Lynn |
| 5,830,547 A | 11/1998 | MacKenzie et al. |
| 6,063,062 A | 5/2000 | Paradis |
| 6,090,082 A | 7/2000 | King et al. |
| 6,162,202 A | 12/2000 | Sicurelli et al. |
| 6,168,576 B1 | 1/2001 | Reynolds |
| 6,241,709 B1 | 6/2001 | Bechtold et al. |
| 6,258,068 B1 | 7/2001 | Kirchhofer et al. |

FOREIGN PATENT DOCUMENTS

| | | |
|---|---|---|
| DE | 3720346 A1 | 12/1988 |
| EP | 0761173 A2 | 3/1997 |
| EP | 0761173 A3 | 7/1997 |

OTHER PUBLICATIONS

Pamphlet by Ferndale Laboratories Inc. "Introducing Applicoater™" 04/04.

UK Patent Office Examination Report Under Section 18(3); UK Appl. No. GB0428458.4; Date: Jun. 24, 2005.

UK Patent Office Examination Report Under Section 18(3); UK Appl. No. GB0428458.4; Date: Apr. 11, 2006.

UK Patent Office Examination Report Under Section 18(3); UK Appl. No. GB0428458.4; Date: Nov. 21, 2005.

* cited by examiner

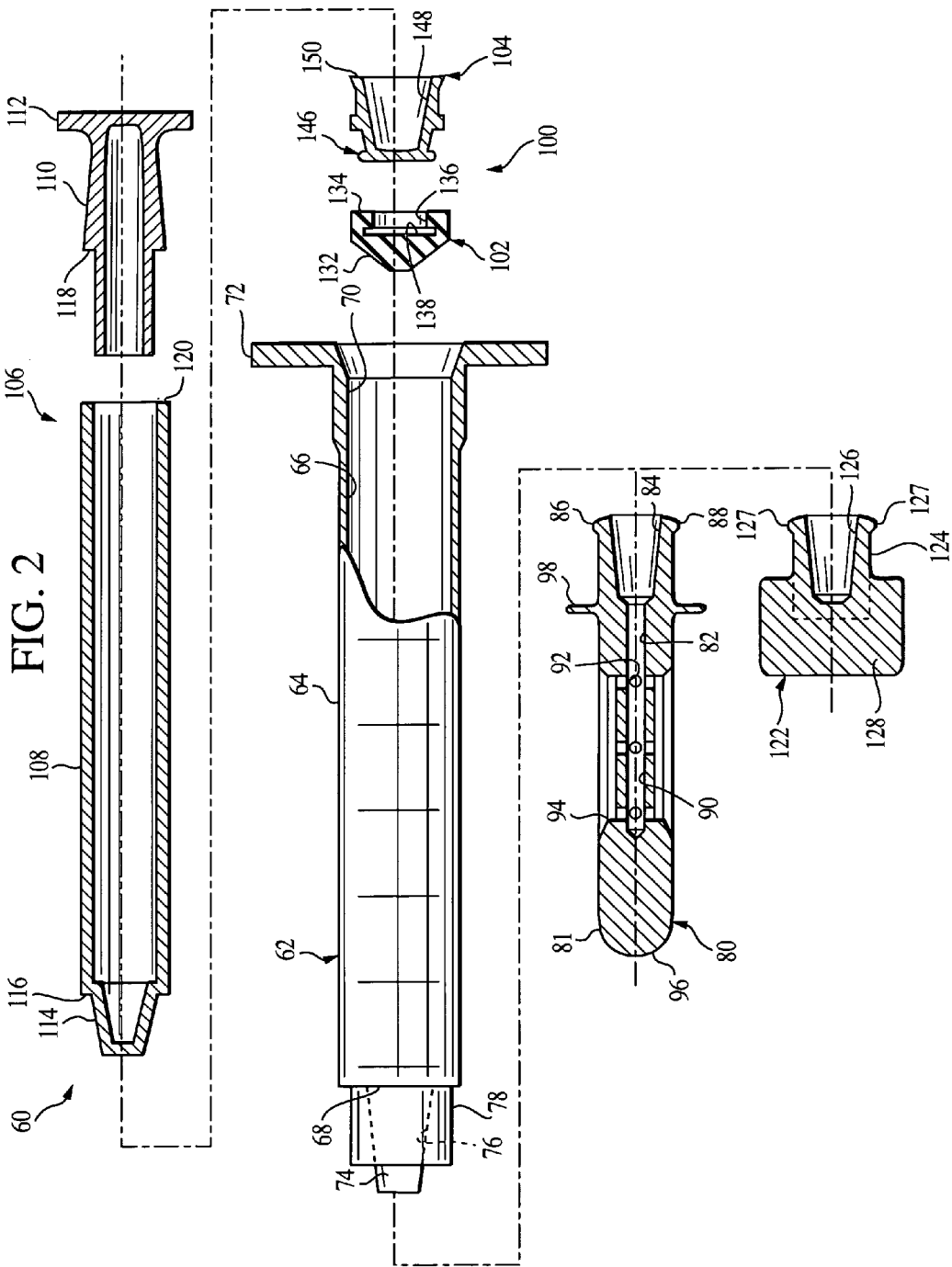

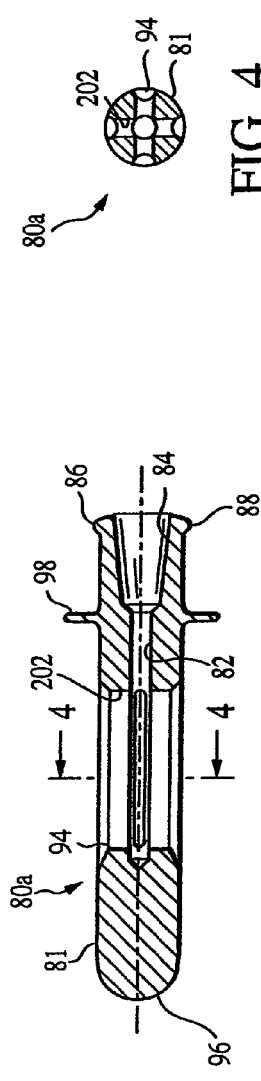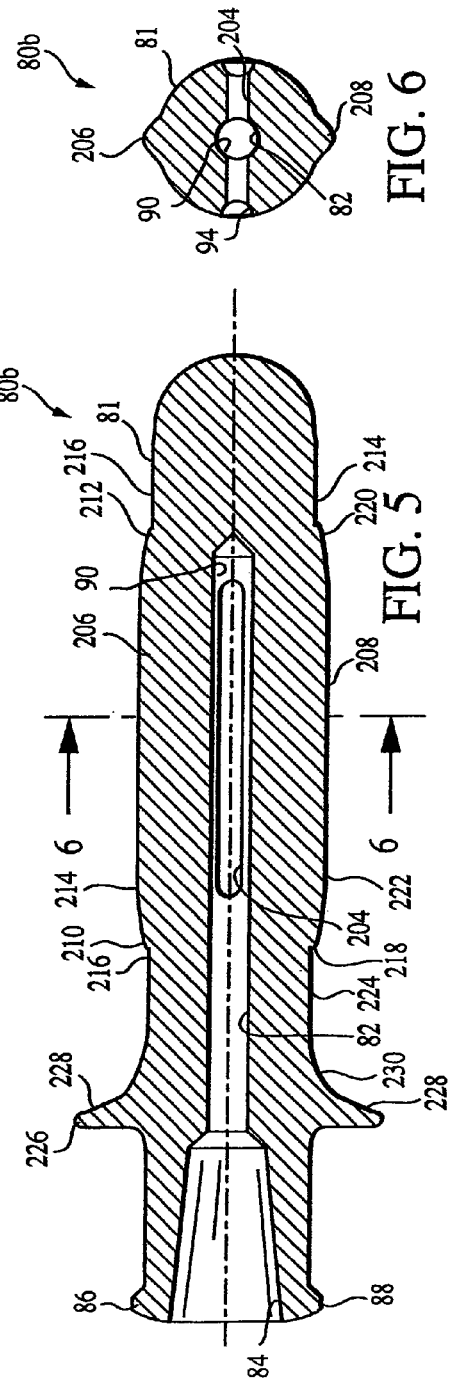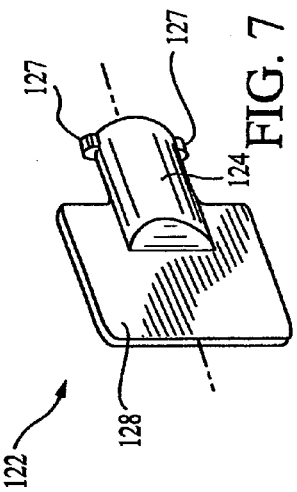

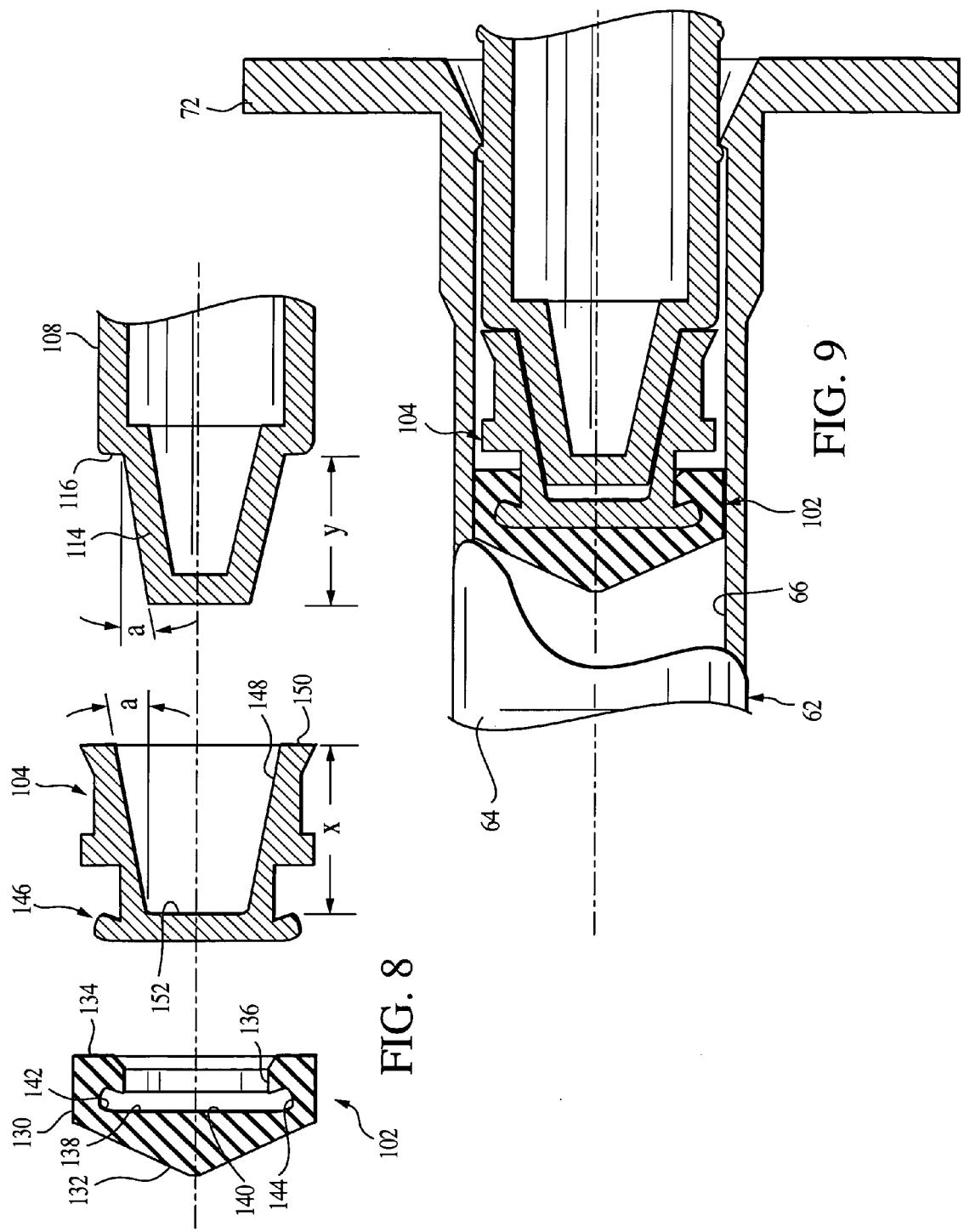

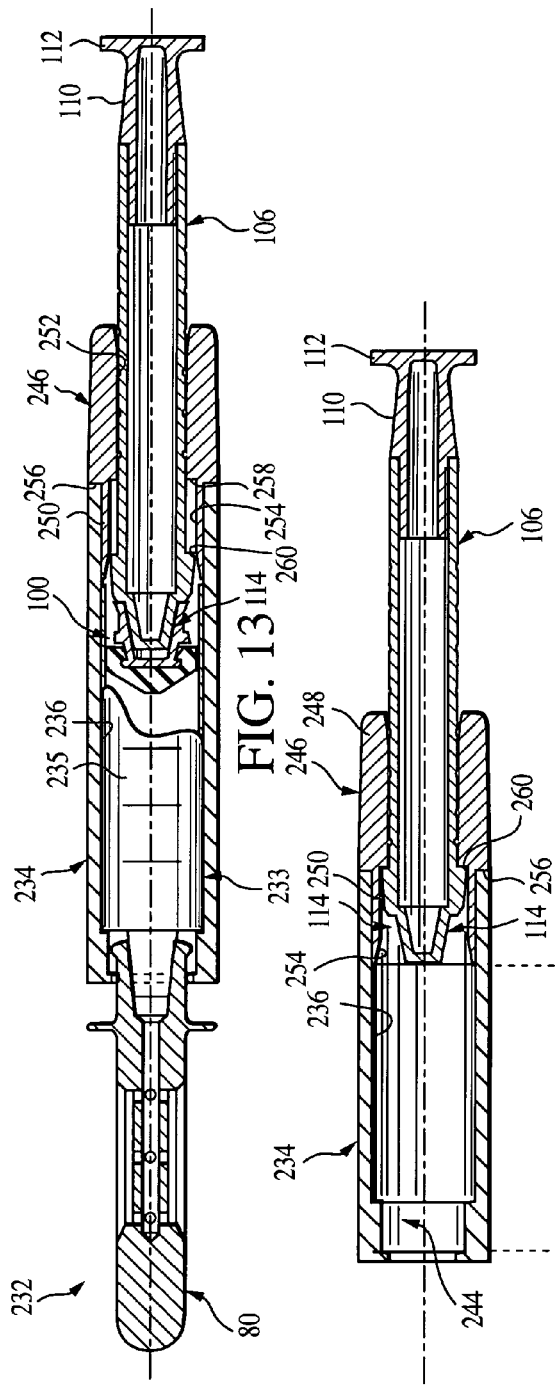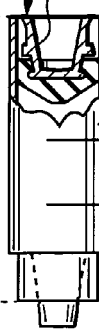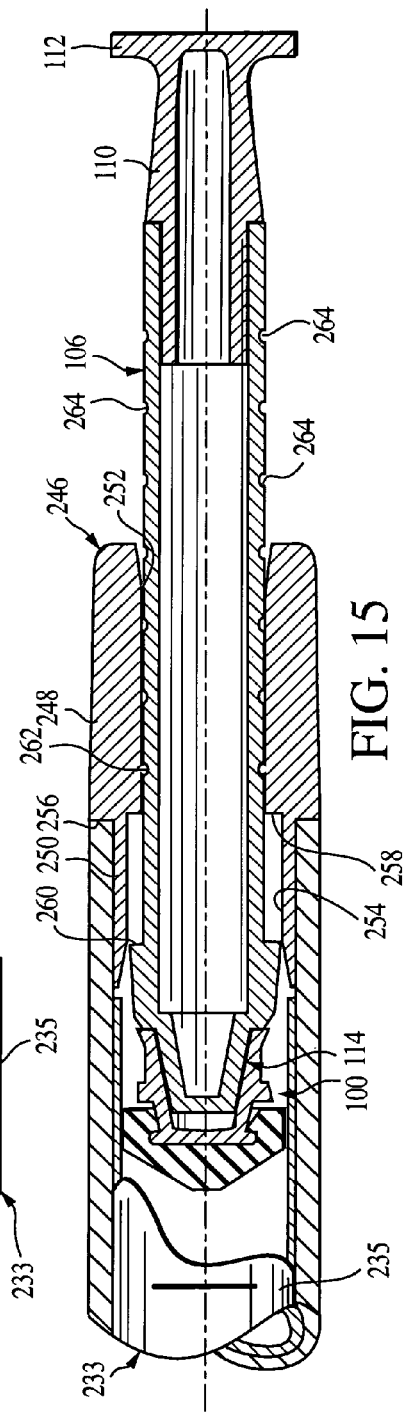

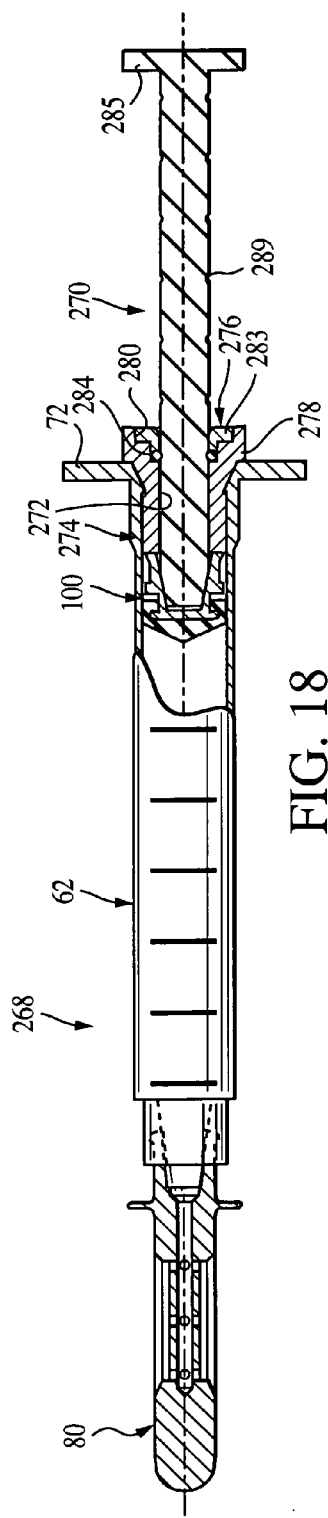
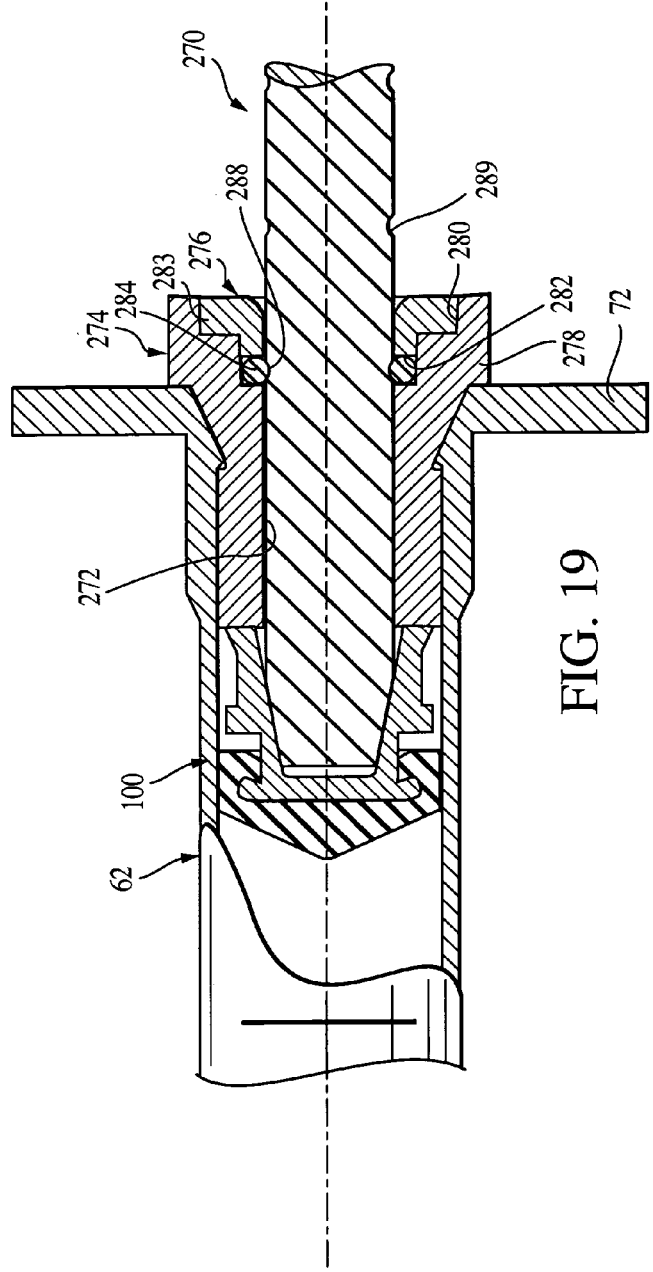
FIG. 18
FIG. 19

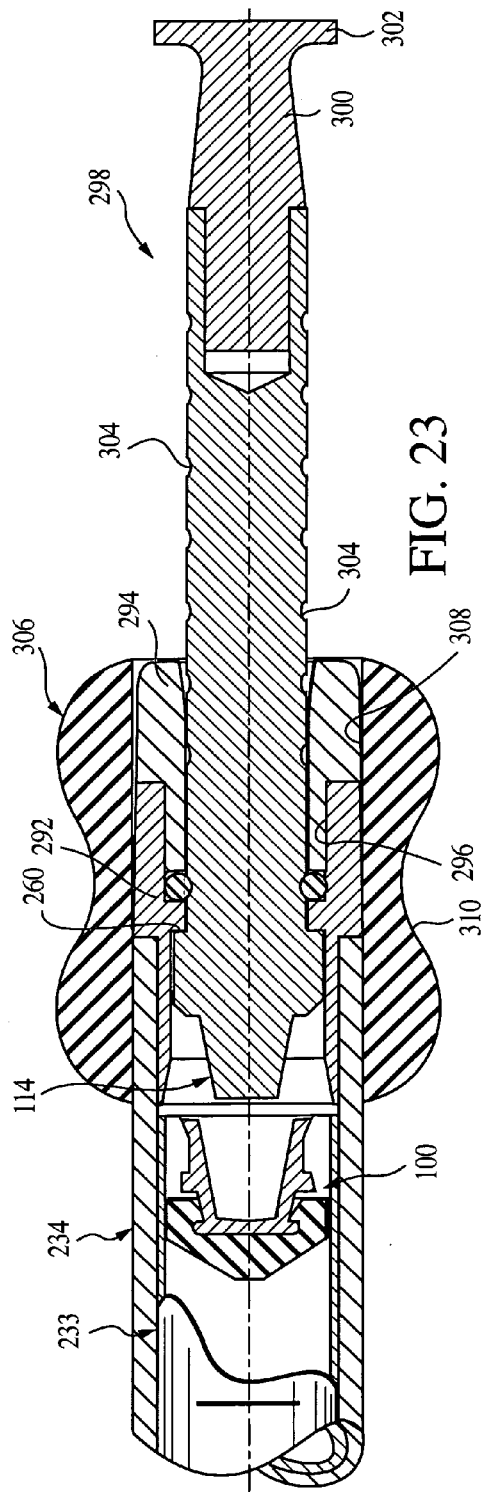
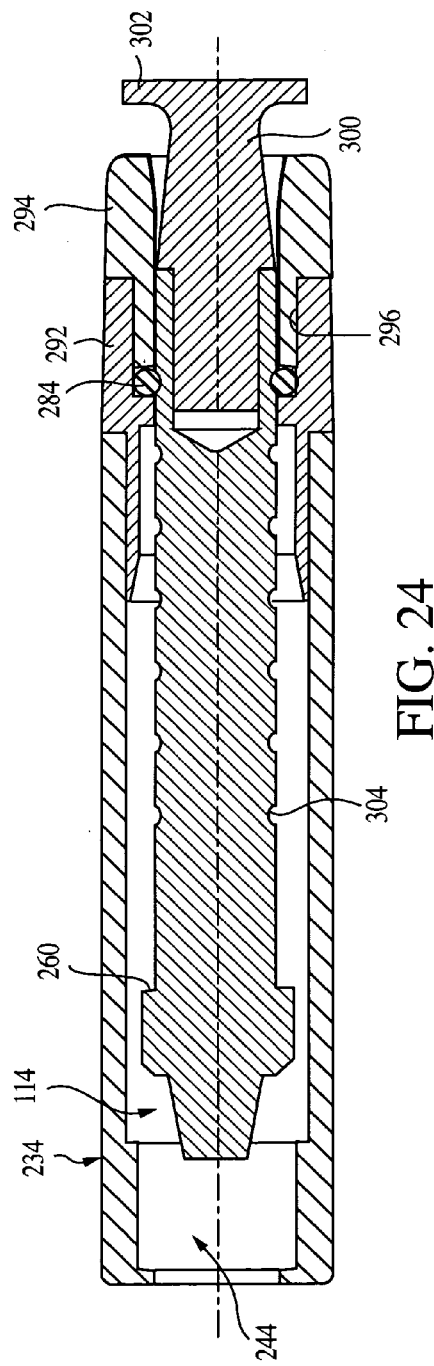
FIG. 23
FIG. 24

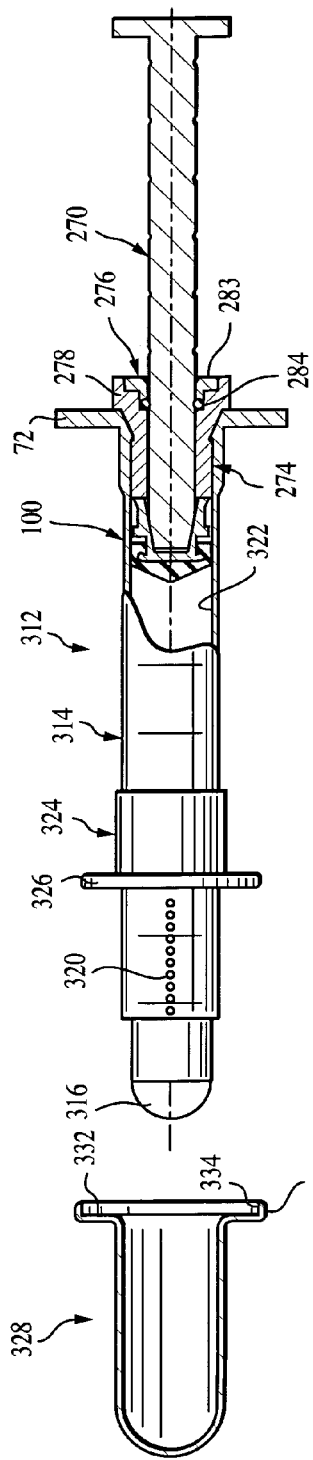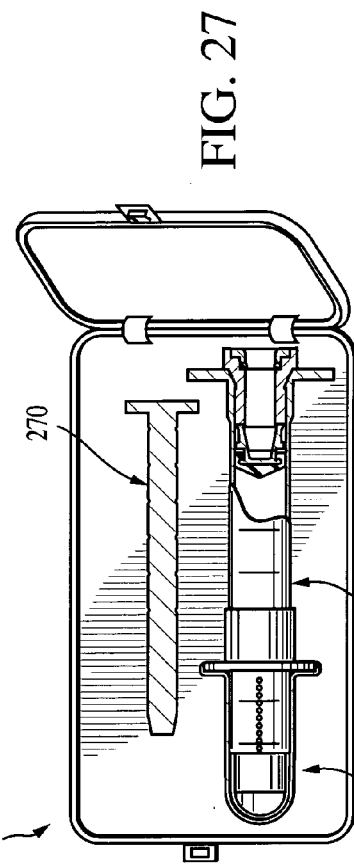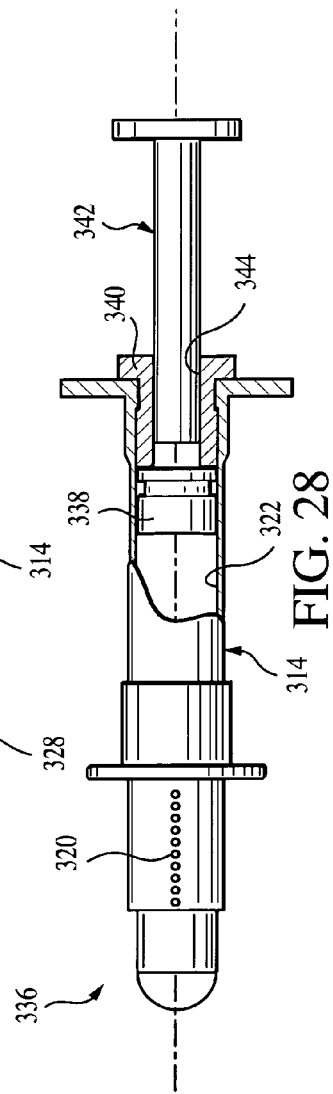

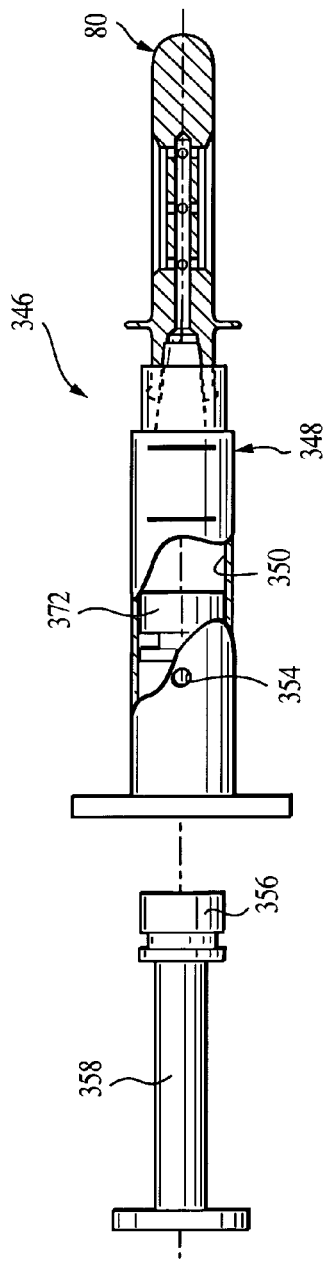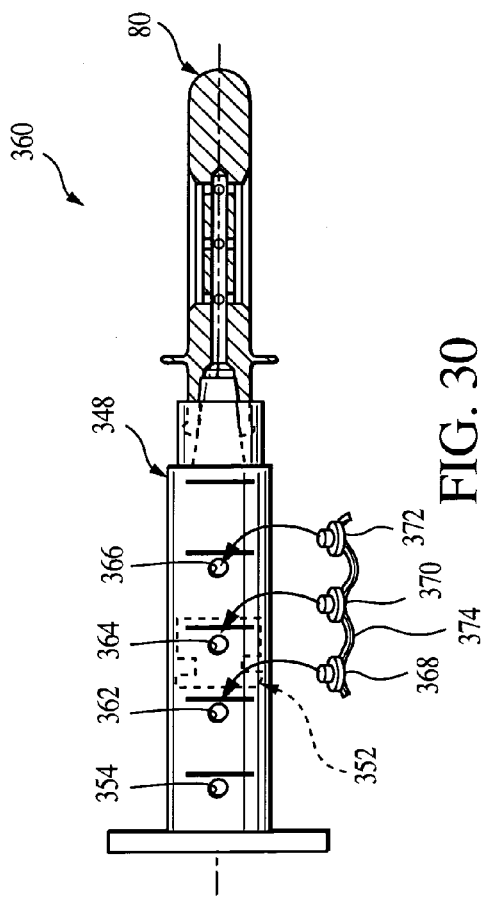
FIG. 29
FIG. 30

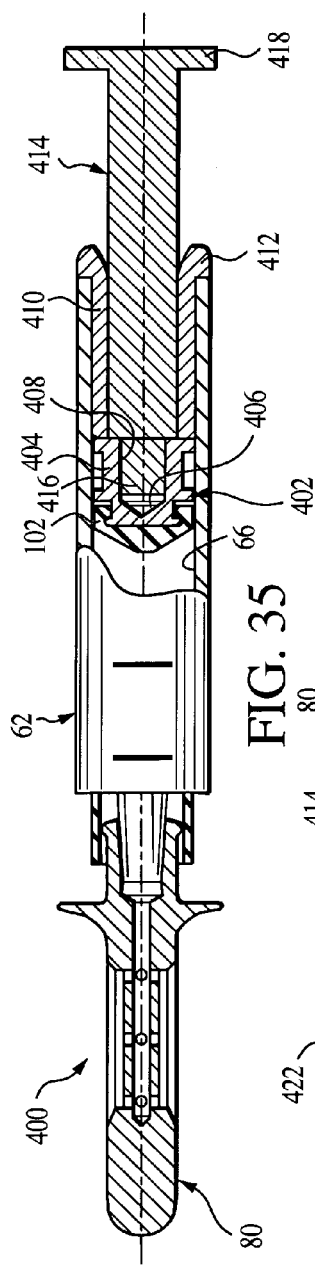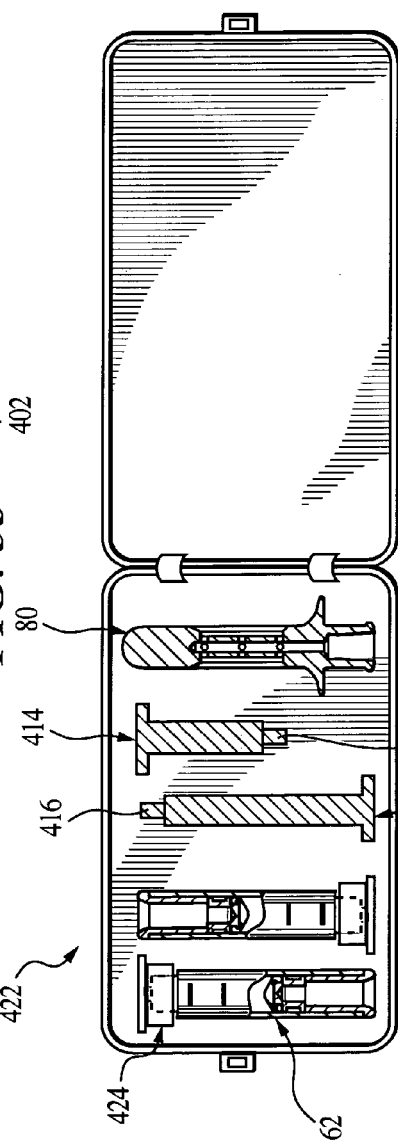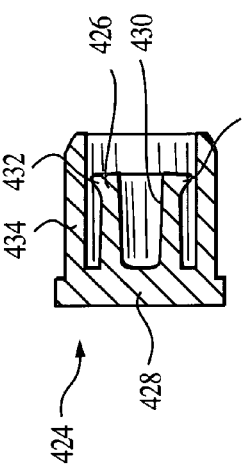

METHODS OF APPLYING A MEDICINAL SUBSTANCE

BACKGROUND OF THE INVENTION

This invention relates to methods of applying a medicinal substance, and particularly relates to methods of applying a medicinal substance onto an area to be treated within a body cavity of a patient.

Various medical conditions, which are located within the vaginal and/or anal openings of the human anatomy, can be treated with medicinal creams and other substances of similar consistency. Frequently, such creams are prescribed by physicians, and are to be applied in measured dosages over a period of time. Because of the necessity for frequent applications of the cream to the affected locations, it is beneficial and economical for the patient to self-administer the measured dosage applications.

However, it is difficult, and in some instances impossible, for the patient to view, or sense, that the proper dosage of the cream is being applied in the vaginal and anal areas. In addition, the act of administering the medicinal cream in such areas, frequently places the patient in awkward physical positions, which require a level of dexterity not inherent in some patients. Under these conditions, imprecise amounts of the cream could be administered undesirably.

In the past, several devices have been developed for storing multiple doses of the medicinal substances within a barrel of a syringe or a cartridge, to facilitate the successive application of time-spaced doses over a period of time. Such devices also include a plunger within the barrel, and a stem for engaging the plunger and urging the cream in successive doses from within the barrel, and through a dispensing means such as an applicator.

Cleanliness of such devices is unpredictable, during dispensing and during storage and transporting thereof. Thus, there is a need for a multiple-dose delivery device which can be easily cleaned while retaining the cream within the barrel, and also during storage and transporting of the device between the time-spaced administering of successive doses of the cream. Also, there is a need for a multiple-dose delivery device which can be dismantled easily for effective cleaning, and for storage and portability.

Other devices developed in the past have included some means for tactile notice to the patient that the appropriate dose has been dispensed. While devices of this type have provided a useful purpose, such devices tend to be complex, costly and, at times, unwieldy. Frequently, the tactile systems of such devices make it difficult, if not impossible, to dismantle the components of the device for cleaning, storage and transporting.

Thus, there is a need for a multiple-dose delivery device which includes an effective tactile system, which is uncomplicated, inexpensive and facilitates the ready dismantling of the components of the device.

Devices developed in the past facilitate the dispensing of the cream generally within the vaginal and/or anal openings, but tend not provide structure which focuses the cream directly onto the critical areas for a most effective treatment.

Thus, there is a need for a multiple-dose delivery device, and an applicator thereof, which focuses the cream directly onto the critical areas to be treated.

SUMMARY OF THE INVENTION

It is, therefore, an object of this invention to provide a focused dosimetry device, which can be easily cleaned while retaining the cream in the cartridge barrel.

Another object of this invention is to provide a focused dosimetry device which can be easily dismantled for effective cleaning, storage and portability.

A further object of this invention is to provide a focused dosimetry device which includes an effective tactile system to inform the patient-user of the accurate dispensing of a prescribed dose of the cream.

An additional object of this invention is to provide a focused dosimetry device with an applicator, and an applicator independently of the device, which focuses the dispensed cream directly onto the critical areas to be treated.

With these and other objects in mind, this invention contemplates a focused dosimetry device which includes a cartridge with a barrel having a passage therethrough between a proximal end thereof and an axially spaced distal end thereof. A plunger head is locatable and movable within the passage of the barrel, and has a compliant section facing the distal end of the barrel and a receptor section facing the proximal end of the barrel. The receptor section is comparatively more rigid than the compliant section. A receptor opening is formed in a proximal end of the receptor section of the plunger head and has a prescribed configuration.

A stem having a stem structure at a proximal end thereof is generally complementary to the prescribed configuration of, and is insertable into, the opening of the receptor. The prescribed configuration is structured to create a piloted engagement of the stem structure within the receptor opening and to preclude a taper-lock interference fit therebetween.

This invention also contemplates a focused dosimetry device, which includes means, located at the distal end of the barrel, for directing a substance from within the barrel to a location outside of the barrel upon movement of the stem toward the distal end of the barrel.

In addition, this invention contemplates a focused dosimetry device which includes a cartridge assembly formed with a barrel having a passage therethrough between a proximal end thereof and an axially spaced distal end thereof. A first tactile structure is located on the cartridge assembly adjacent the proximal end of thereof, and a compliant plunger is locatable and movable within the passage of the barrel. A stem having a distal end is positionable within the barrel to facilitate movement of the plunger within the barrel.

A plurality of second tactile structures are located spatially on the stem in a position to engage successively the first tactile structure on the cartridge assembly as the stem is moved into the barrel to provide tactile notification of delivery of measured amounts of a substance from within the barrel.

Further, this invention contemplates a focused dosimetry device, which includes an applicator attached to a distal end of a cartridge of the device and has a body which is formed with an axial passage in communication with the barrel of the cartridge. The axial passage of the applicator extends from a proximal end of the body toward a closed distal end thereof. A plurality of elongated slots are formed spatially and radially through the body in communication with the axial passage and an exterior of the body.

Still further, this invention contemplates an applicator for dispensing a substance therethrough, which includes a body formed with an axial passage having an entry opening at a proximal end of the body for receiving the substance to be dispensed. The axial passage of the applicator extends from the proximal end of the body toward a closed distal end thereof. A plurality of elongated slots are formed spatially, with respect to each other, and radially through the body in communication with the axial passage and an exterior of the body. Each of the elongated slots is formed with a corresponding elongated outlet, for passing the substance from the entry opening, through the axial passage, the plurality of elongated slots, and the respective elongated outlets to the exterior of the body. The applicator may also include a wiper for disbursing and spreading the cream about the critical area to be treated, and also a tactile flange having a concave frustoconical surface for a comfortable indication of the proper depth of insertion of the applicator.

Additionally, this invention contemplates a focused dosimetry device, which includes a cartridge formed with a barrel having a passage therethrough between a proximal end thereof and an axially spaced distal end thereof. The cartridge has an exterior shape of a prescribed configuration. A plunger head is locatable and movable within the passage of the barrel. A stem has a distal end positionable within the barrel to facilitate movement of the plunger within the barrel A carrier formed with a cartridge-receiving nest has a shell-like opening which is generally complementary to the prescribed configuration of the exterior shape of the cartridge. Means is provided for retaining the cartridge within the cartridge-receiving nest. A guide extends from a proximal end of the carrier and is formed with a passage for receiving at least an intermediate portion of the stem for sliding movement of the intermediate portion therein. Means is provided for precluding removal of the distal end of the stem from within the carrier.

Also, this invention contemplates a focused dosimetry device and case for storing and for portability of the components of the device when not in use.

Other objects, features and advantages of the present invention will become more fully apparent from the following detailed description of the preferred embodiment, the appended claims and the accompanying drawings.

BRIEF DESCRIPTION OF THE DRAWINGS

In the accompanying drawings:

FIG. 2 is an exploded side view showing components of the focused dosimetry device of FIG. 1, including a first embodiment of an applicator, and a first embodiment of a cap, all in accordance with certain principles of the invention;

FIG. 3 is a sectional side view showing a second embodiment of an applicator, in accordance with certain principles of the invention;

FIG. 4 is a sectional view taken along lines 4—4 of FIG. 3 showing internal details of the second embodiment of the applicator of FIG. 3, in accordance with certain principles of the invention;

FIG. 5 is a sectional view showing a third embodiment of an applicator, in accordance with certain principles of the invention;

FIG. 6 is a sectional view taken along line 6—6 of FIG. 5 showing the third embodiment of the applicator of FIG. 5, in accordance with certain principles of the invention;

FIG. 7 is a perspective view showing the cap of FIG. 2 for assembly with the focused dosimetry device of FIG. 2, and other embodiments of focused dosimetry devices described herein, in accordance with certain principles of the invention;

FIG. 8 is an exploded view showing a plunger head, with a plunger, or plunger section, and a receptor section, and further shows a distal end of a stem, all of the focused dosimetry device of FIGS. 1 and 2, in accordance with certain principles of the invention;

FIG. 9 is a partial sectional view showing the assembly of the plunger, the receptor section and the distal end of the stem of FIG. 8 located within the proximal end of a cartridge syringe barrel of the focused dosimetry device of FIGS. 1 and 2, in accordance with certain principles of the invention;

FIG. 13 is a sectional side view showing a second embodiment of a focused dosimetry device, including a carrier, in accordance with certain principles of the invention;

FIG. 14 is a sectional side view showing assembled components of the carrier of FIG. 13 in position for receiving a cartridge in accordance with certain principles of the invention;

FIG. 15 is a partial sectional view showing various components of the focused dosimetry device of FIG. 13 in assembly, in accordance with certain principles of the invention;

FIG. 18 is a partially-sectioned side view showing a third embodiment of a focused dosimetry device, in accordance with certain principles of the invention;

FIG. 19 is a partially-sectioned side view showing various components of the focused dosimetry device of FIG. 18 in assembly, in accordance with certain principles of the invention;

FIG. 23 is a sectional view showing various components of the focused dosimetry device of FIG. 21 in assembly, in accordance with certain principles of the invention;

FIG. 24 is a sectional side view showing components of the focused dosimetry device of FIG. 21, including the carrier and a stem, in an assembled condition for storage of the device, in accordance with certain principles of the invention;

FIG. 25 is a side view showing a fifth embodiment of a focused dosimetry device, in accordance with certain principles of the invention;

FIG. 26 is a side view of a cover for use with the focused dosimetry device of FIG. 25, in accordance with certain principles of the invention;

FIG. 27 is a top view showing disassembled components of the focused dosimetry device of FIG. 25 stored within complementarily shaped nests of a case for storage of the components when the device is not in use, in accordance with certain principles of the invention;

FIG. 28 is a partially-sectioned side view showing a sixth embodiment of a focused dosimetry device, in accordance with certain principles of the invention;

FIG. 29 is a partially-sectioned side view showing a seventh embodiment of a focused dosimetry device, in accordance with certain principles of the invention;

FIG. 30 is a partially-sectioned side view showing an eighth embodiment of a focused dosimetry device, in accordance with certain principles of the invention;

FIG. 35 is a partially-sectioned side view showing a tenth embodiment of a focused dosimetry device for use with two stems, in accordance with certain principles of the invention;

FIG. 36 is a top view showing disassembled components of the focused dosimetry device of FIG. 25, including two stems of different lengths, stored within complementarily shaped nests of a case for storage of the components when the device is not in use, in accordance with certain principles of the invention;

FIG. 37 is a section view showing a second embodiment of a cap for assembly with the focused dosimetry device of FIG. 35, and other embodiments of focused dosimetry devices described herein, in accordance with certain principles of the invention;

DETAILED DESCRIPTION OF THE INVENTION

In the embodiments of the focused dosimetry devices as described below, a substance, such as medicinal cream, compound, or the like, is deposited into a barrel of a cartridge of the device. The volume of the cream deposited in the cartridges of the respective embodiments represents a single dose or multiple doses, depending on the particular embodiment being used or described. With respect to the devices which contain multiple doses of the cream, several single doses can be administered successively therefrom over a period of time, and the components of the multiple dose devices can be disassembled, cleaned, stored and/or transported, if desired or necessary, during periods when the device is not being used.

The consistency of the cream is such that the cream does not flow easily within or out of the cartridge without a force being applied to the barrel-confined mass thereof. Typically then, a plunger head within the barrel is urged by pushing a stem, which is in contact with the head, to force the cream to exit the barrel.

The focused dosimetry devices described below are particularly useful for applying and focusing each administered dose of cream to affected areas of vaginal and anal openings of the human anatomy. The devices, or portions thereof, may be useful for other purposes without departing from the spirit and scope of the invention.

Each below-described focused dosimetry device includes a dispensing end at which the cream is dispensed from the cartridge to the affected area of the patient. Such dispensing end of each focused dosimetry device will hereinafter be referred to as the distal end. The opposite end of each such device, which includes a stem, will be referred to as the proximal end of the device. The end of any component of each focused dosimetry device, which is closest to the distal end of the device, will be referred to as the distal end of the component, and the other end of such component, which is opposite the distal end, will be referred to as the proximal end.

Figure 1:
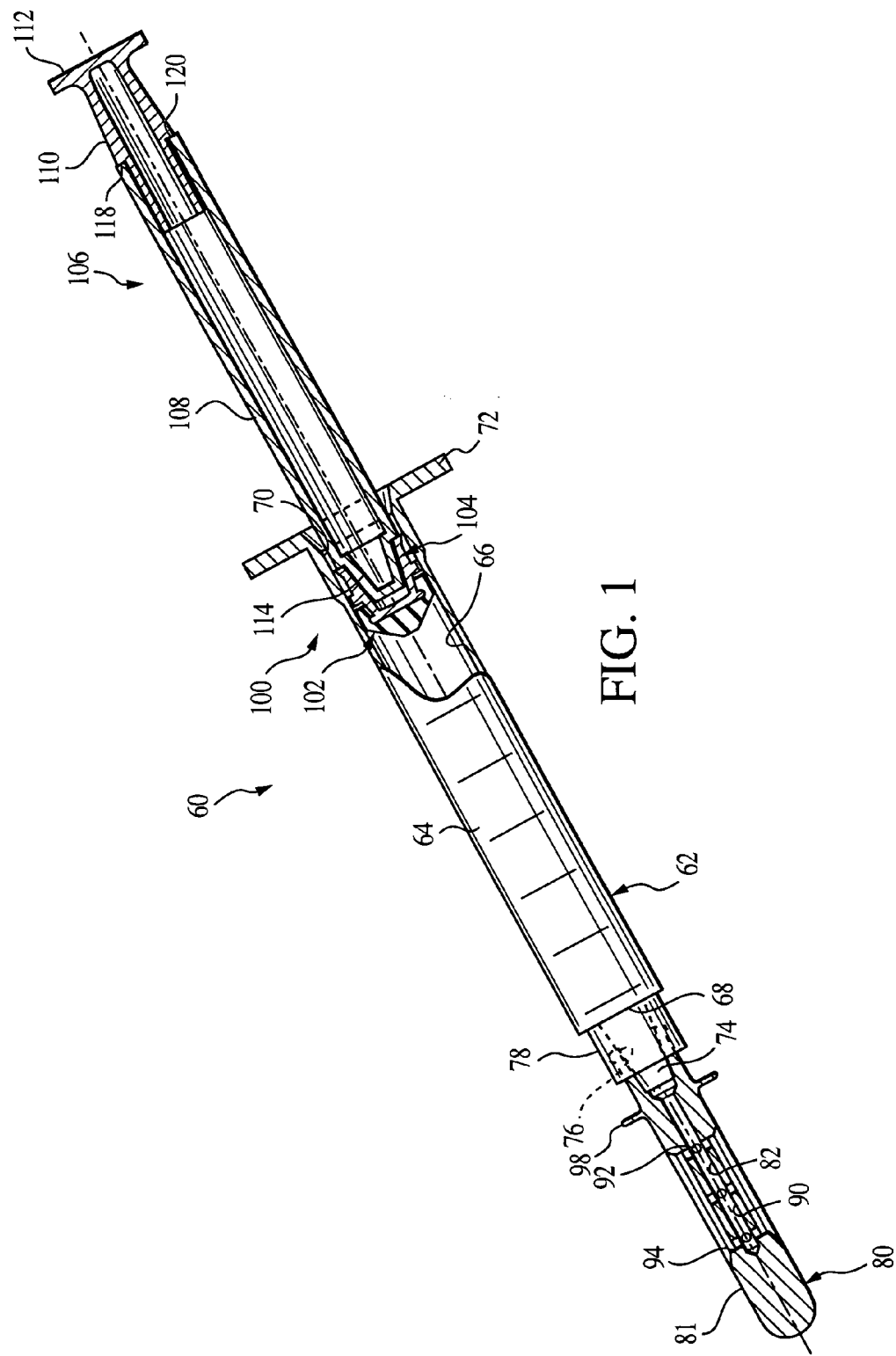
FIG. 1 is a partially-sectioned side view showing a first embodiment of a focused dosimetry device, in accordance with certain principles of the invention.

Referring to FIGS. 1 and 2, a first embodiment of a focused dosimetry device is identified as device 60, and is typically used in multiple dose applications. The device 60 includes a cartridge 62, having a barrel 64, for containing a substance such as the medicinal cream, or any other substance having a cream-like consistency. The device 60 is a multiple dose device. However, certain principles of the invention embodied in the device 60 could be used in a single does device.

In the device 60, the barrel 64 is formed with a hollow interior barrel passage 66, having a distal opening 68 at a distal end thereof and a proximal opening 70 at proximal end thereof. A finger-rest flange 72 is formed radially outward on the barrel 64 at the proximal end thereof.

A small-diameter sleeve 74 forms an integral part of the cartridge 62, and is in axial alignment with the barrel 64 at the distal end thereof, and forms a sleeve passage 76, which is in communication with the barrel passage 66. The exterior of the small-diameter sleeve 74 is tapered in the form of a frustum, with the smaller diameter of the frustum located at the distal end of the sleeve, and the axis of the frustum being coincidental with the axis of the barrel 64.

A large-diameter sleeve 78 also forms an integral part of the cartridge 62, at the distal end thereof, and is in axial alignment with the barrel 64, and coaxial alignment with the small-diameter sleeve 74. An internal cylindrical wall of the large-diameter sleeve 78 is threaded, and the proximal end of the sleeve is closed and not in communication with the barrel passage 66.

An applicator 80, or tip, which is formed with a smooth body 81 having an axial passage 82 therein, is assembled with the cartridge 62 at the distal end of the barrel 64, for example, by use of a known coupling facility such as the coupling facility identified with U.S. registered trademark LUER-LOC.

In particular, as shown in FIG. 2, the axial passage 82 of the applicator 80 is formed with a tapered proximal opening 84 which mates with the exterior taper of the sleeve 74 of the cartridge 62 to facilitate one aspect of the attachment of the applicator with the cartridge. The body 81 of the applicator 80 is formed with a first ear 86 and a second ear 88, which extend in radially opposite directions from the proximal end of the applicator. Upon assembly of the applicator 80 with the cartridge 62, the outboard ends of the ears 86 and 88 are threadedly applied to, and within, the large-diameter sleeve 78 by rotation of the applicator. The rotation of the applicator 80 also enhances the tapered assembly of the tapered small-diameter sleeve 74 with the tapered proximal opening 84 of the axial passage 82.

It is noted that facilities, other than as described above, can be used to attach the applicator 80 to the cartridge 62 without departing from the spirit and scope of the invention. Such attachment facilities could be threaded, unthreaded, tapered, press fit, or the like.

As shown in FIGS. 2 and 4, the applicator 80 is further formed with an inner passage 90, four axially-aligned, equally angularly spaced sets of three axially-spaced radially-oriented holes 92 in each set, and four axially-elongated slot-like outer openings 94. The tapered proximal opening 84, the inner passage 90, the holes 92 and the openings 94 of the applicator 80 are all in communication with each other to facilitate the smooth flow of the cream from the barrel 64 and through the applicator.

The applicator 80 is formed with a rounded distal end 96 and a tactile-indicator flange 98 near the proximal end thereof. The rounded distal end 96, and the smooth applicator body 81, provide a user-friendly applicator. The flange 98 provides a tactile indication to the patient that the applicator 80 has been inserted into the vaginal or anal cavity at the appropriate distance for placement of the openings 64 adjacent the areas to be treated with the cream.

Referring again to FIGS. 1 and 2, a plunger head 100 includes a compliant section, also referred to as a compliant plunger 102, which is locatable and movable within the passage 66 of the barrel 64. The plunger head 100 also includes a receptor section 104 which is coupled to the plunger 102. The plunger head 100 is assembled for sliding movement within the passage 66 of the barrel 64, between the proximal opening 70 and the distal opening 68 of the barrel.

A hollow rigid stem 106, which, for example, could be composed of a thermoplastic material such as polycarbonate, is formed by a secured assembly of a stem member 108 and a thumb piece 110, which is formed at the proximal end thereof with a flange-like thumb rest 112. The stem member 108 is formed with a stem structure 114 at a closed distal end thereof, with the stem structure being in the shape of a frustum. The distal end of the stem 106 is initially inserted into the proximal opening 70 of the barrel 64 such that the stem structure 114 engages a proximal end of the receptor section 104 of the plunger head 100. This provides facility for urging the plunger head 100 within the passage 66 of the barrel 64, toward the distal end thereof.

The diameter of the proximal end of the stem structure 114 of the stem 106 is smaller than the diameter of the stem member 108, thereby forming a shoulder 116 at the junction of the stem structure and the stem member. Also, a shoulder 118 is formed radially on an intermediate portion of the thumb piece 110, which abuts a proximal end 120 of the stem member 108 upon assembly of the stem member and the thumb piece, whereafter the thumb piece and the stem member are bonded together.

Figure 12:
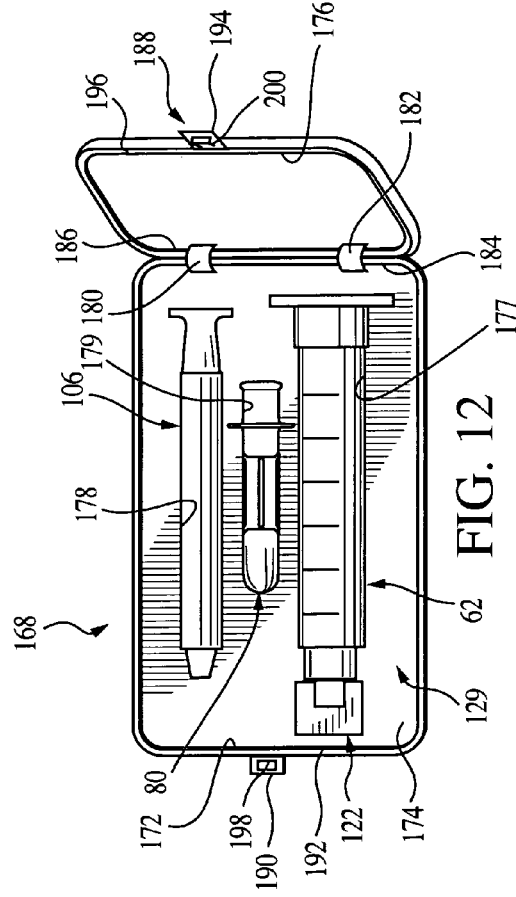
FIG. 12 is a top view showing disassembled components of the focused dosimetry device of FIGS. 1 and 2 stored within complementarily shaped nests of a case for storage of the components when the device is not in use, in accordance with certain principles of the invention.

During periods when the device 60 is not being used, the applicator 80 is removed from assembly with the cartridge 62. A first embodiment of a cap 122, as shown in FIGS. 2 and 7, is attached in place of the applicator 80 to seal the distal opening 68 of the barrel 64 to prevent cream from discharging or leaking undesirably from the barrel. The cap 122 is formed with a cylindrical cup 124, which is formed with a tapered opening 126 for receipt of the tapered small-diameter sleeve 74 when assembling the cap with the cartridge. A pair of ears 127 are formed radially outward at the proximal end of the cup 124. A flat vane 128 is formed integrally with a closed end of the cup 92 to facilitate handling of the cap 122 during assembly and disassembly of the cap with respect to the sleeve 74. The assembly of the cartridge 62 and the cap 122 forms a cartridge-cap assembly 129, as shown in FIG. 12.

Referring now to FIGS. 8 and 9, the plunger 102 is formed from a compliant or elastomeric material such as, for example, butyl rubber or buna rubber. The plunger 102 is formed with an outer peripheral surface 130 having a diameter which is sized to fit within the passage 66 of the barrel 64, to allow sliding axial movement of the plunger within the passage. The cream is typically stored within a storing portion of the passage 66 between a distal end 132 of the plunger 102 and the distal end of the passage. The sliding fit of the plunger 102 within the passage 66 will also preclude the flow of cream from the storing portion of the passage, past the plunger and toward the proximal end of the barrel 64.

The distal end 132 of the plunger 102 is formed with a shallow taper to an axial point thereof pointing toward the distal end of the barrel 64. A proximal end 134 of the plunger 102 is formed with an opening 136, of a first diameter, which communicates with a comparatively larger cavity 138, of a second diameter. The cavity 138 is formed axially farther within the plunger 102 toward the distal end 132 thereof, where the second diameter is greater than the first diameter. The cavity 138 is formed with a flat floor 140, with an axially short side wall 142, which is contiguous with the floor, and is angled radially outward and toward the proximal end 134 of the plunger 102. The cavity 138 is formed with an axially longer side wall 144, which is contiguous with the short side wall 142, and is angled radially inward and toward the proximal end 134 of the plunger 102.

The receptor section 104 of the plunger head 100 is composed, for example, of a thermoplastic material such as acetal, and is rigid in comparison to the compliant plunger 102. The receptor section 104 is formed with a structure 146 which is complementary with the hollow structure of the combined profile of the opening 136 and the cavity 138 to facilitate coupling assembly of the receptor section with the plunger to form the plunger head 100 as illustrated in FIG. 9.

A receptor opening 148 is formed in a proximal end 150 of the receptor section 104 of the plunger head 100 and is formed with a prescribed configuration. In particular, with reference to FIG. 8, the receptor opening 148 is formed with a tapered side wall at a taper angle "a," and at a depth of "x" to a floor 152. The stem structure 114 of the stem 106 is formed in a configuration similar to the prescribed configuration of the receptor opening 148, the only difference being that the stem structure extends for a distance "y" from the stem member, which is less than the depth "x" of the receptor opening. Because of the difference in the depth "x" and the distance "y," the distal end of the stem structure 114 does not engage the floor 152 of the receptor opening 148 when the stem structure is assembled fully within the receptor opening, as shown in FIG. 9. This allows the stem structure 114 to fully seat within the receptor opening 148 without interfering engagement between the floor 152 of the receptor opening 148 and the distal end of the stem structure 114.

When the stem structure 114 is being assembled with the plunger head 100, the matching taper of the stem structure and the receptor opening 148 facilitates a piloting engagement thereof. During this process, the stem structure 114 and the receptor opening 148 cooperate quickly to locate the optimum interfacing engagement thereof in preparation for the application of a force to the stem 106 to move the plunger head 100 toward the distal end of the barrel 64.

When engaging surfaces of two objects having the same taper are moved axially together, the angle of such taper plays a part in the manner in which the surfaces interface with each other. Based, to some extent, on the materials of the two objects in the area of the interfacing surfaces, there is a critical angle of taper below which the interfacing surfaces engage with a taper-lock interference fit. In order to release the two objects from such an interference fit, considerable force must be used to pull the objects apart, which tends to disturb the location of both objects. If the taper is above the critical angle, the interfacing surfaces do not engage in a taper-lock interference fit, and a first of the objects can be moved easily away from a second of the objects without disturbing the location of the second object.

The critical taper angle consideration is important in the operation of the multiple dose device 60, and other multiple dose embodiments described herein, because, in multiple dose situations, the stem 106 is removed from assembly with the plunger head 100 following the application of each dose. It is important that the plunger head 100 remain in its end-of-dose position after each dose is administered so that the plunger head will be in the appropriate position for the initiation of the next dose to be administered. If there had been a taper-lock interference fit between the stem structure 114 and the wall of the receptor opening 148, considerable force would have been required to separate the stem structure from within the receptor opening, which would have resulted in undesirable movement of the plunger head 100. This is particularly so with respect to the device 60, and other multiple dose embodiments described herein, because there is no way to grasp and hold steady the plunger head 100 while removing the stem 106. Also, the plunger head 100 is, in essence, floating in a lubricated environment provided by the cream contained within the barrel 64, which would tend to ease and enhance the undesirable movement of the plunger head when the stem 106 being removed.

Based on the above described structure of the device 60, the prescribed configuration of the taper angle "a" is structured to create a piloted engagement of the stem structure 114 within the receptor opening 148 and to preclude a taper-lock interference fit.

Figure 10:
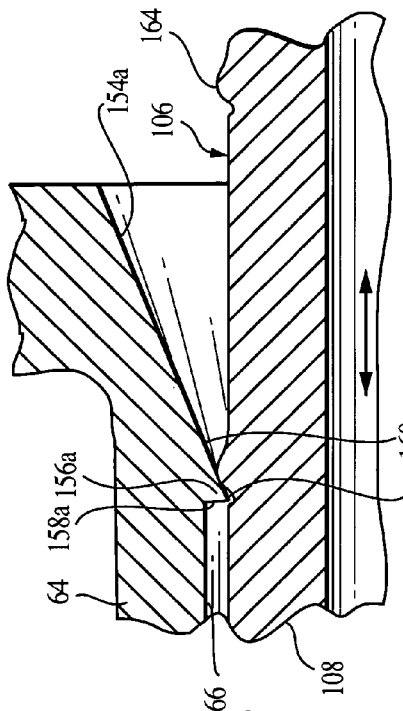
FIG. 10 is a partial sectional view showing a first embodiment of a tactile registration system for facilitating measured relative movement between the stem and the cartridge barrel of FIG. 2 of the focused dosimetry device of FIGS. 1 and 2, in accordance with certain principles of the invention.

Referring to FIG. 10, the proximal opening 70 of the barrel 64 is formed with a funnel-shaped surface 154 which extends radially inward and toward the distal end of the barrel. An internal annular rib 156, which is a first tactile structure located on the cartridge 62 adjacent the proximal end thereof, is formed at a juncture of the surface 154 and the wall surface of the passage 66 of the barrel 64. The rib 156 is formed with a radial surface 158 and a sloping surface 160 which join at a pointed edge 162.

A plurality of annular ribs 164, which are a plurality of second tactile structures, are located spatially on the stem 106 in position to engage the rib 156, that is, the first tactile structure, of the cartridge 62 as the stem is moved into the barrel 64 to provide delivery of measured amounts of the substance from within the barrel. A slight annular depression 166 is formed on the distal side of each of the plurality of annular ribs 164 for accommodation of the pointed edge 162.

The spacing between each adjacent pair of the plurality of annular ribs 164 correlates to the dispensing of a single dose of the multiple doses of cream initially contained within the cartridge 62. As one of the plurality of ribs 164 moves into engagement with the rib 156, the opposition to continued movement of the stem 106 is sensed by the patient-user as a tactile response to indicate that the dispensing of a single dose of the cream has been completed. The opposition to movement of the stem 106, presented by the engagement by one of the ribs 164 with the rib 156, is easily overcome, when the next single dose is to be dispensed, but clearly serves as tactile notification to the patient-user that each successive single dose has been administered.

Figure 11:
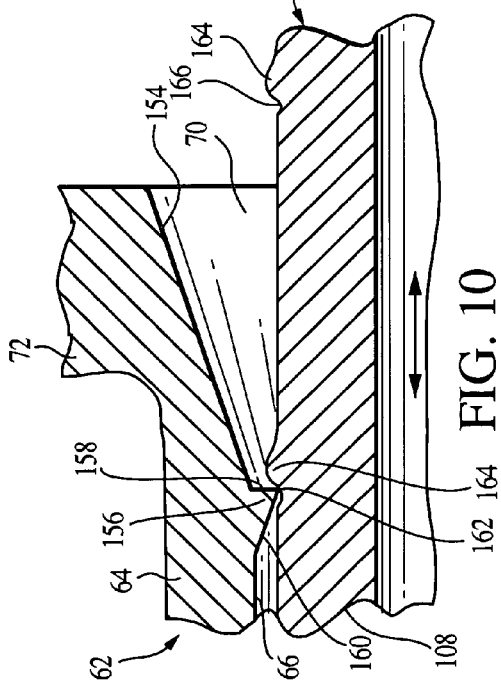
FIG. 11 is a partial sectional view showing a second embodiment of a tactile registration system for facilitating measured relative movement between the stem and the cartridge barrel of FIG. 2 of the focused dosimetry device of FIGS. 1 and 2, in accordance with certain principles of the invention.

Referring to FIG. 11, another embodiment of a tactile system includes structure similar to the structure illustrated in FIG. 10. In particular, in FIG. 11, the orientation of the rib 156 (FIG. 10) has been reversed to form a rib 156*a* with a sloping surface 160*a* being a continuation of a funnel-shaped surface 154*a*. A radial surface 158*a* is formed between a pointed edge 162*a* and the wall surface of the passage 66. The structure of the stem 106 and the plurality of ribs 164, in the embodiment of FIG. 11, is unchanged.

In operation of the multiple dose device 60, the cartridge 62, with the appropriate multiple dose volume of cream, is delivered to the patient-user. The device 60 is delivered with the cap 122 attached to the distal end of the cartridge 62, and with the plunger head 100 located at the proximal end of the cream within the cartridge. In this condition, the cream is captured between the capped distal end of the cartridge 62 and the distal end of the plunger head 100, and cannot escape.

When the patient-user is preparing to administer the first of the multiple doses contained in the cartridge 62, the cap 122 is removed and the applicator 80 is attached to the distal end of the cartridge. The distal end of the stem 106 is then inserted into the passage 66 of the barrel 64 at the proximal end thereof, and the stem structure 114 is moved into the receptor opening 148 to seat the stem structure in the opening, in the manner described above. The patient-user then places the applicator 80 into the body opening to be treated. The patient-user senses the initial insertion of the flange 98 into the cavity as tactile notification that the applicator 80 is in the appropriate location for administering the cream. The patient-user pushes the stem 106 toward the distal end of the cartridge 62, whereby the first dose of cream is dispensed from the applicator 80 onto the area to be treated.

Eventually, tactile notification is sensed by the patient-user when one of the ribs 164 of the stem 106 engages the rib 156 of the cartridge 62, in the manner described above. The applicator 80 is then removed from the cavity. During the dispensing of the first dose of the cream, the plunger head 100 has been moved to a position at which the dispensing of the second dose will begin.

The stem 106 is removed, with ease as described above, without disturbing the position of the plunger head 100. The applicator 80 is removed from the distal end of the cartridge 62. All of the separated components can be cleaned, if needed or desired. The cap 122 is attached to the distal end of the cartridge 62, which forms the cartridge-cap assembly 129 having a prescribed cartridge-cap profile. Also, an exterior of the stem 106 has a prescribed stem profile, and an exterior of the applicator 80 has a prescribed applicator profile.

Referring to FIG. 12, a case 168 includes a first compartment 172 with a base surface 174, and a second compartment 176. The base surface 174 of the first compartment 172 is formed with a plurality of nests 177, 178 and 179 in configurations of any one, or more, of the prescribed cartridge-cap profile, the prescribed stem profile and the prescribed applicator profile, respectively. The first compartment 172 is coupled to the second compartment 176 by hinges 180 and 182 along adjacent edges 184 and 186, respectively, of the first and second compartments. The case 168 is integrally formed by a plastic molding process, whereby the hinges 180 and 182 are formed integrally with the first compartment 172 and the second compartment 176, respectively.

A latch arrangement 188 includes a first element 190, which is formed on a first edge 192 of the first compartment 172, and a second element 194, which is formed on a second edge 196, opposed to the first edge 192, of the second compartment 176. The first element 190 is formed with an opening 198, and the second element 194 is formed with a latch projection 200, which snaps into the opening 198 to latch the first compartment 172 with the second compartment 176 when the first and second compartments are moved in closing engagement about the hinges 180 and 182. The latch projection 200 is formed with a camming surface, which cams the projection through the opening 198, and a shelf, which snaps under the first element 190 adjacent the opening 198 to latch the first compartment 172 with the second compartment 176.

Thus, this structure forms the latch arrangement 188 which is located on opposing edges 192 and 196 of the first and second compartments 172 and 176, respectively, for coupling engagement when the first and second compartments are closed on each other.

After separating the applicator 80 and the stem 106 from the cartridge 62, and after placing the cap 122 onto the distal end of the cartridge, the patient-user places the cartridge-cap assembly 129, the stem and the applicator into their respective nests 177, 178 and 179, respectively, of the case 168. The second compartment 176 is then closed over the first compartment 172, and latched in a closed position by the latch arrangement 188.

The patient-user can then store the case 168 in a convenient location, or transport or carry the case with them, in anticipation of the next single dose to be administered.

With respect to the descriptions below of other embodiments of the focused dosimetry devices, including the applicators and the cases, the description of preceding embodiments will not be repeated where the components of such later-described embodiments are identical to the described components of the preceding embodiments. Also, the numerals used in a preceding description will be used in the later description to identify the identical components.

Referring to FIGS. 3 and 4, a second embodiment of an applicator, identified as applicator 80*a*, is formed with four equally, angularly and axially-elongated through slots 202 in place of the holes 62 of the applicator 80. Otherwise, the applicator 80*a* is identical to the applicator 80, and is assembled with the cartridge 62 in the same manner described above with respect to the applicator 80. The axially-elongated through slots 202 of the applicator 80*a* provide a faster and more widespread application of the cream to the affected area to be treated in comparison to the delivery through the holes 92 of the applicator 80.

Referring to FIGS. 5 and 6, a third embodiment of an applicator, identified as applicator 80*b*, and which is the preferred embodiment, is similar to the applicator 80. For example, each of the applicators 80 and 80*b* is formed with the smooth body 81 having the axial passage 82 therein, and is to be assembled with the cartridge 62 at the distal end of the barrel 64. Also, the applicator 80*b* is formed with the axial passage 82, with a tapered proximal opening 84, which mates with the exterior taper of the sleeve 74 of the cartridge 62 to facilitate one aspect of the attachment of the applicator with the cartridge. The body 81 of the applicator 80*b* is formed with the first ear 86 and the second ear 88, which extend in radially opposite directions from the proximal end of the applicator, to facilitate assembly of the applicator 80b with the cartridge 62 in the manner described above with respect to the applicator 80.

In addition, the body 81 of the applicator 80b is formed with the two diametrically-opposed axially-elongated through slots 204, which, individually, are identical to the through slots 202 of the applicator 80a. The applicator 80b is also formed with two wipers 206 and 208 which extend radially outward from diametrically opposite sides of the body 81 of the applicator 80b, and which extend axially and parallel to the through slots 204. The through slots 204 and the two wipers 206 and 208 are equally angularly spaced about the axis of the body 81, as shown in FIG. 4. Each of the two wipers 206 and 208 extend radially outward from the body 81 in the shape of a convex mound.

A first pair of ramps 210 and 212 are formed with, and extend axially in opposite directions from, opposite ends of the wiper 206, and extend from a radially outwardmost surface 214 of the wiper to respective adjacent surface portions 216 of the body 81. A second pair of ramps 218 and 220 are formed with, and extend axially in opposite directions from, opposite ends of the wiper 208, and extend from a radially outwardmost surface 222 of the wiper to respective adjacent surface portions 224 of the body 81.

The applicator 80b is also formed with a tactile-indicator flange 226 which functions in similar fashion as the flange 98 of the applicator 80, as described above. A distal side of the flange 226 of the applicator 80b is formed with a straight portion 228, which extends toward the axis of the applicator and toward the distal end thereof. A shallow concave portion 230 of the flange 226 extends between the straight portion 228 and the outer surface of the body 81.

When a patient-user uses the applicator 80b, the body 81 is inserted into the vaginal or anal opening of the patient until the patient tactilely senses engagement with the flange 226, in the manner noted above with respect to the use of the applicator 80. With the combined straight portion 228 and the concave portion 230 on the distal side of the flange 226, a gentile and gradual engagement of the flange with the patient is accomplished to avoid discomfort to the patient during the process.

In the same manner noted above with respect to the applicator 80a, the axially-elongated through slots 202 of the applicator 80b provide a faster and more widespread application of the cream to the affected area to be treated. After the cream has been applied within the vaginal or anal opening, the focused dosimetry device 60, including the applicator 80b, can be rotated and/or oscillated about the applicator axis. With such action, the wipers 206 and 208 of the applicator 80b engage the deposited cream, and spread the cream about, and wipe the cream into, the affected area, to provide an effective application of the cream.

As the patient inserts the applicator 80b into, or removes the applicator from, the vaginal or anal openings, the ramps 210, 212, 218 and 220 provide a comfortable transition for those areas of the patient which must transition from the smooth outer surface of the body 81 to the outwardmost surfaces 214 and 222 of the wipers 206 and 208, respectively. If the ramps 210, 212, 218 and 220 were not present, the patient would sense an abrupt and uncomfortable reaction to engagement with the ends of the wipers 206 and 208.

While the applicator 80b is the preferred embodiment, any of the three applicators 80, 80a and 80b can be used with the cartridge 62, as well as other cartridges described below, without departing from the spirit and scope of the invention. Further, any of the three applicators 80, 80a and 80b form a means located at the distal end of the barrel 64 for directing a substance from within the barrel to a location outside of the barrel upon movement of the stem 106 toward the distal end of the barrel.

As illustrated in FIG. 5, the body 81 of the applicator 80b is formed about a longitudinal axis, and with the axial passage 82. The axial passage 82 includes an entry port 201 at a proximal or first end of the axial passage. A dispensable substance, such as the above-noted cream, can be moved through the entry port 201 and into the axial passage 82. The axial passage 82 extends axially longitudinally from the entry port 201 toward the closed distal end 96 of the body 81, and to a closed distal, or second, end 203 of the axial passage, by a predetermined passage distance. Each of the slots 204 is formed laterally or radially through the body 81, and is coincidental with an intermediate section 205 of the axial passage 82. Also, each of the slots 204 is in communication with the intermediate section 205 of the axial passage 82 and is contiguous with an outer surface of the body 81. This structural arrangement facilitates the dispensing of the cream from the intermediate section 205 of the axial passage 82 to an exterior area adjacent the outer surface of the body 81, and particularly onto an area to be treated within a body cavity of a patient.

Each of the slots 204 is elongated and extends axially longitudinally by a prescribed slot distance, or slot length, from a proximal end 207 of the slot to a distal or second end 209 of the slot. The pair of slots 204 represent a plurality of elongated circumferentially-spaced slots formed radially through the body 81 and extending in an axial direction in communication with the intermediate section 205 of the axial passage 82 and the exterior of the body.

A proximal section 211 of the axial passage 82 extends axially longitudinally by a prescribed proximal distance, or proximal length, from the entry port 201 to a location immediately adjacent the proximal ends 207 of the slots 204, but does not overlap the proximal ends 207. A distal section 213 of the axial passage 82 extends axially longitudinally by a prescribed distal distance, or distal length, from the closed distal, or second, end 203 of the axial passage 82 to a location immediately adjacent the distal ends 209 of the slots 204, but does not overlap the distal ends 209.

As further illustrated in FIG. 5, the proximal length of the axial passage 82 is less that the slot length of the slots 204, and is greater than the distal length of the axial passage.

The intermediate portion 205 of the axial passage 82, which is immediately adjacent and in communication with the slots 204, represents a defined space. In addition, the defined space can be provided by a container having an internal defined volume, with an entry opening for depositing the mass of the substance therein, and an exit opening for facilitating dispensing at least portions of the mass of the substance therefrom. The defined space of the intermediate portion 205 of the axial passage 82, as well as the container, can also be considered an elongated defined space.

As also illustrated in FIG. 5, a proximal or first side 225 of the tactile-indicator flange 226 is radially aligned with the entry opening 201 of the axial passage 82. Further, the angled straight portion 228 and the concave curved portion 230 of the distal or second side of the flange 226 blend to form a contoured surface. As noted above, the body 81 is closed at the distal end 96 thereof, which prevents antegrade inflow leakage of the cream from the axial passage 82, or container, farther into the body cavity beyond the defined space, in a direction away from the external opening. It is noted that the body cavity could be an anal cavity, a vaginal cavity, or any cavity of the body in which the cream is to be administered.

The outer surface, or exterior, of the body 81 of the applicator 80b, as illustrated in FIGS. 5 and 6, is cylindrical in shape from the junction of the curved portion 230 of the flange 226 and the outer surface, and extends in the cylindrical shape to the distal end 96 of the body. In addition, the axial passage 82 is cylindrical in shape from the first end 201 to the second end 203 of the axial passage. It is noted that the outside surface and the axial passage of each of the applicators 80 and 80a, as illustrated in FIGS. 1 through 4, are also cylindrical in shape.

As noted above, the distal side of the flange 226, including the straight portion 228 and the curved portion 230, will tactilely engage the anatomical area of a self-administering patient to notify the patient that the slots 204 of the applicator 80b, or the exit opening of the container, have been located adjacent the area to be treated. Thus, the flange 226, and the distal side thereof, provide a means, responsive to locating the slots 204, or the exit opening of the container, adjacent the area to be treated by a self-administering patient, for notifying the patient that each of the slots, or the exit opening of the container, is located adjacent the area to be treated.

When a patient is to self-administer the cream onto the area of the body cavity to be treated, the proximal end of the applicator 80b is assembled with the distal end of the cream-containing cartridge 62 by using any of the attachment techniques described above. Thereafter, the patient inserts the closed, rounded, distal end 96 of the applicator 80b, or the container, through the external opening of the body cavity. The patient continues to move trailing portions of the applicator, or the container, into the body cavity, whereby the applicator, or container, can move apart any interfacing portions of the body cavity which may be in the path of movement of the applicator, or container, into the body cavity.

Eventually, the defined space, as described above, is established at a location within the body cavity, which is spaced from the external opening of the body cavity at least by the prescribed proximal distance. The cream is formed in a mass externally of the body cavity such as, for example, in the cartridge 62. The mass of cream is then moved from the cartridge 62 and into the defined space of the axial passage 82 of the prepositioned applicator 80b, or the prepositioned container. Thereafter, at least portions of the mass of cream, adjacent the slots 204, or exit opening of the container, are moved, or urged, from the defined space onto the area to be treated within the body cavity.

The mass of the cream, which is moved into the defined space from the cartridge 62, is shaped in an elongated form of the elongated defined space, and is moved in a direction of elongation of the elongated form of the mass. Prior to moving the at least portions of the mass of the cream through the slots 204, or the exit opening of the container, the mass is maintained within the elongated defined space in the elongated form by the confinement of the applicator 80b, or the container.

The self-administering patient continues to move the applicator 80b, or the container, into the body cavity until being tactilely notified by the flange 226, or similar structure of the container, that the slots 204, or exit opening of the container, have been placed adjacent the area to be treated.

After the cream, or substance, has been deposited onto the area to be treated, the self-administering patient may rotate the applicator 80b, by rotating the cartridge 62, for providing a more uniform dispersal of the cream onto the area to be treated, prior to withdrawal of the applicator from the body cavity.

While the foregoing description has been directed toward the self-administration of the cream into the body cavity by the patient, as the user, it is to be understood that administering of the cream into the body cavity of the patient could be accomplished by a caregiver or a user other than the patient. Therefore, the "user" could be the patient or someone other than the patient. In the event that the user is someone other than the patient, the non-patient user would be tactilely notified when the contoured surface of the flange 226 engages the area around the external opening of the body cavity.

Further, while the foregoing description is directed to the applicator 80b, the applicators 80 and 80a include structure which functions in the manner of the applicator 80b. For example, as shown in FIGS. 1 through 4, applicators 80 and 80a are formed with a body having an axial passage, and with slots which communicate with the axial passage. The slots of the applicators 80 and 80a are contiguous with the outer surface of the body, and each of the applicators is formed with a tactile flange which is radially aligned with the entry end of the axial passage.

The foregoing description has been directed to the use of the applicator 80b for the application of the medicinal cream onto areas to be treated within the body cavity of the patient. It is to be understood that the applicator 80b, as well as the applicators 80 and 80a, can be used for the application of a substance into a body cavity of the human anatomy for purposes other than medicinal.

Referring to FIGS. 13, 14 and 15, a second embodiment of a focused dosimetry device, identified as device 232, is typically used in multiple dose applications. The device 232 includes a cartridge 233, the applicator 80 and the stem 106. The cartridge 233 is similar to the cartridge 62, but is not formed with a finger-rest flange 72 at the proximal end thereof. The plunger head 100 is contained within a barrel 235 of the cartridge 233, and the stem 106 is formed with the stem structure 114, which is in complementary assembly within the receptor opening 148 in the manner described above.

Figure 16:
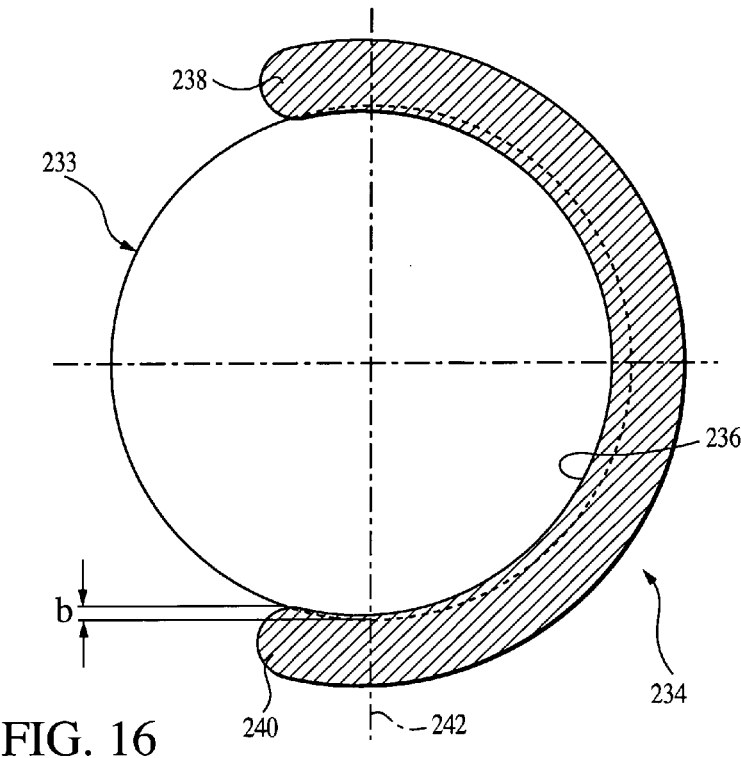
FIG. 16 is an end view showing the cartridge of FIG. 14 in assembly with the carrier of the focused dosimetry device of FIG. 13, in accordance with certain principles of the invention.

Referring particularly to FIG. 14, a carrier 234 is formed with a cartridge-receiving nest 236 having a shell-like opening which is generally complementary to the prescribed configuration of the exterior shape of the cartridge. As shown in FIG. 16, the nest 236 is formed in a C-shaped configuration having end portions 238 and 240, which extend past a vertical centerline 242. The cartridge 233 is shown in the nest 236, with the end portions 238 and 240 slightly about adjacent portions of the cartridge by a distance "b," to provide a means for retaining the cartridge 233 within the cartridge-receiving nest 236, which can be overcome only by an external force applied to the cartridge.

Referring again to FIG. 14, a distal end of the nest 236 is formed with a stepped wall 244 which is complementary to the axial structural profile of the distal end of the cartridge 233. The stepped wall 244 precludes the cartridge 233 from moving forward of the distal end of the carrier 234 when the cartridge is seated within the nest 236.

A guide 246 is formed with an enlarged cylindrical section 248 extending over approximately a proximal one-half of the axial length thereof, and a reduced cylindrical section 250 which extends approximately a distal one-half of the axial length of the guide. In addition, the guide 246 is formed with an axial passage 252 which ultimately receives at least an intermediate portion of the sleeve 106 for sliding movement of the intermediate portion therein. The axial passage 252 includes a passage chamber 254 at the distal end thereof.

The guide 246 is also formed with a radially outward shoulder 256 which abuts a distal end of the carrier 234 upon assembly therewith, and a radially inward shoulder 258, which abuts a shoulder 260 formed at the proximal end of the stem structure 114 of the stem 106, when the stem is moved to its farthest proximal location.

Prior to forming the device 232, the carrier 234, the guide 246, the stem 106, and the thumb piece 110 are in an unassembled state. The proximal end of the stem 106 is inserted into the passage chamber 254 of the guide 246, at the distal end thereof, and through the axial passage 252 until the stem shoulder 260 abuts the inward shoulder 258 of the guide. The thumb piece 110 is assembled within the proximal end of the stem 106, and is secured in that position, by bonding, gluing or any suitable process. The reduced cylindrical section 250 of the guide 246 is inserted into the opening of the carrier 234 at the proximal end thereof, and is secured in that position.

As shown in FIG. 14, the carrier 234, the guide 246 and the stem 106 are now in assembly, with the stem being slidable within the axial passage 252, but otherwise captured with the carrier and the guide. The stem 106 can be pulled in a proximal direction until the stem shoulder 260 engages the inward shoulder 258 of the guide 246, thereby providing a means for precluding removal of the distal end of the stem from within the carrier 234. Also, the stem 106 can be moved in a distal direction until the underside of the thumb rest 112 engages a proximal end of the guide 246.

As shown particularly in FIG. 15, an internal annular rib 262, which is a first tactile structure, is formed on the guide 246 and extends radially-inward thereof-within the axial passage 252. A plurality of annular grooves 264, which are a plurality of second tactile structures, are located spatially axially on the stem 106 in position to engage the rib 262, that is, the first tactile structure of the guide 246, as the stem is moved into barrel 64 to provide delivery of measured amounts of the substance from within the barrel.

The spacing between each adjacent pair of the plurality of annular grooves 264 correlates to the dispensing of a single dose of the multiple doses of cream initially contained within the cartridge 233. As one of the plurality of grooves 264 moves into engagement with the rib 262, the opposition to continued movement of the stem 106 is sensed by the patient-user as a tactile response to indicate that the dispensing of a single dose of the cream has been completed. The opposition to movement of the stem 106, presented by the engagement by the rib 262 with one of the grooves 264, is easily overcome, when the next single dose is to be dispensed, but clearly serves as tactile notification to the patient-user that each successive single dose has been administered.

When the focused dosimetry device 232 is to be used, the patient-user insures that the stem 106 is fully positioned in the proximal direction as shown in FIG. 14. The cap 122 is removed from the distal end of the cartridge 233, and the applicator 80 is attached to the distal end of the cartridge as described above. The cartridge 233 is then inserted into the nest 236 of the carrier 232, and snapped into place in the nest by virtue of the circumferentially extended end portions 238 and 240 of the carrier. The device 232 is now in condition to be used.

The patient-user places the applicator 80 within the vaginal or anal opening and pushes the stem 106 in the distal direction. Eventually, the rib 262 engages next one of the annular grooves 264 to provide tactile indication that one measured dose of the cream has been delivered.

The applicator 80 is removed from the patient-user and the stem 106 is then moved fully in the proximal direction, as shown in FIG. 14, and the cartridge 233 is removed from the nest 236. The applicator 80 is detached from the distal end of the cartridge 233, and the cap 122 is attached in place of the applicator.

Figure 17:
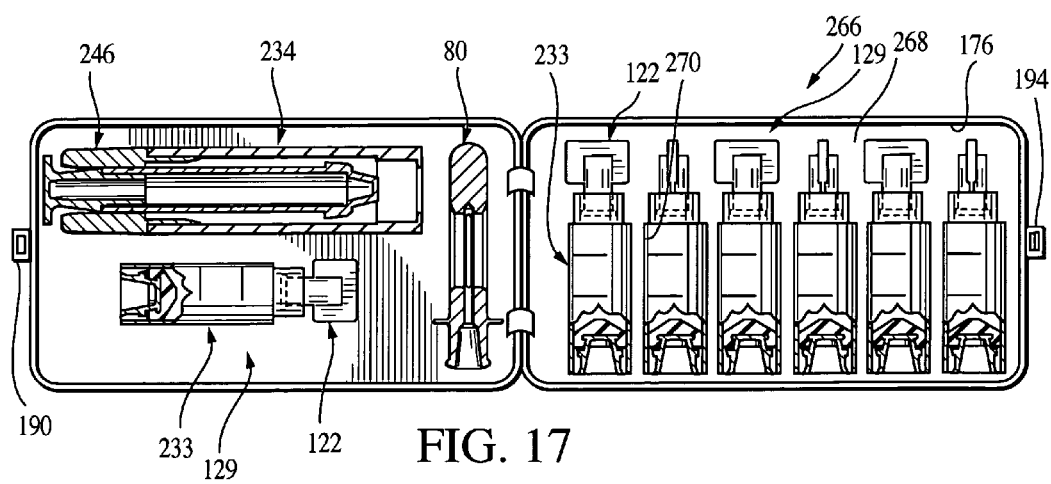
FIG. 17 is a top view showing disassembled components of the focused dosimetry device of FIG. 13 stored within complementarily shaped nests of one compartment of a two-compartment case for storage of the components when the device is not in use, and a plurality of the cartridges of FIG. 14 stored within complementarily shaped nests, in accordance with certain principles of the invention.

After cleaning, the patient-user then places the disassembled components of the device 232 into respective nests of a case 266, shown in FIG. 17. It is noted that the formation of the nests of the case 266 are complementary to the profiles of the various components stored therein, in the same manner as in the above-described case 168 (FIG. 12). Further, the second compartment 176 of the case 266 is formed with a base surface 268 in which a plurality of nests 270 are formed for receipt of a plurality of cartridge-cap assemblies 129.

In this manner, the capped cartridge 233, which is being used during an extended period for dispensing the multiple doses, is stored in the first compartment 172, along with the applicator 80 and the assembly of the carrier 234 and the stem 106. At the same time, a supply of filled cartridge-cap assemblies 129 is stored in the second compartment. This arrangement allows the patient-user to carry the case 266 for ready access of the additional, filled cartridge-cap assemblies 129, when the cream of the initial cartridge 233 has been dispensed.

Figure 20:
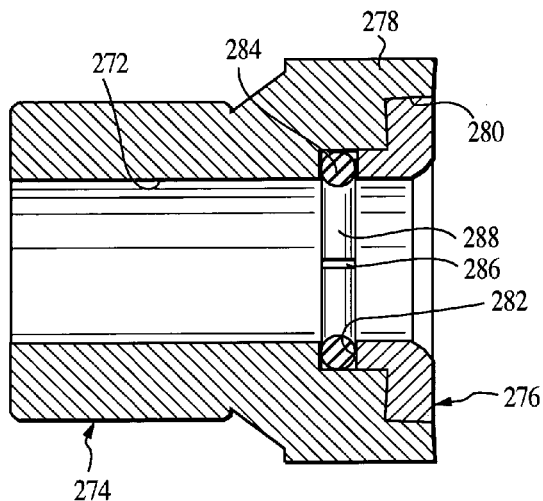
FIG. 20 is a sectional view showing a first guide and a second guide which form components of the focused dosimetry device of FIG. 18, in accordance with certain principles of the invention.
Figure 21:
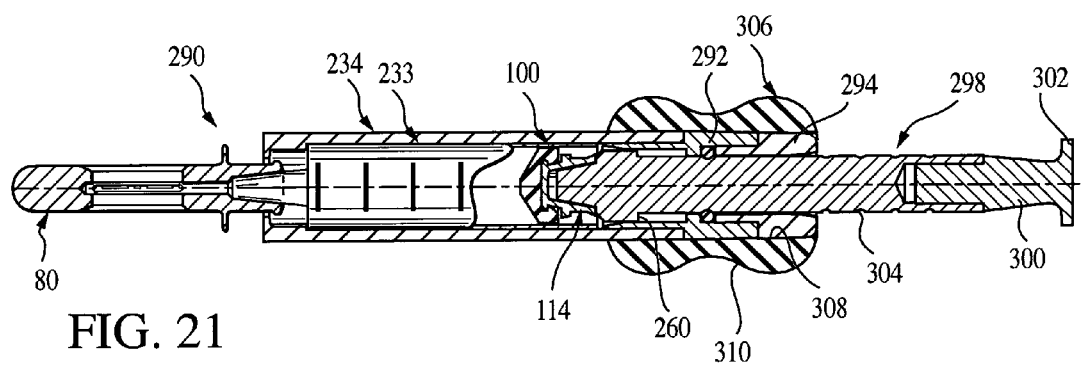
FIG. 21 is a side view showing a fourth embodiment of a focused dosimetry device, including a carrier, tactile structures and a finger rest, in accordance with certain principles of the invention.

Referring to FIGS. 18, 19 and 20, a third embodiment of a focused dosimetry device, identified as device 268, is similar to the device 60 as shown in FIGS. 1 and 2, and is typically used in multiple dose applications. The differences reside in a stem 270, which is solid as compared to the two-piece hollow stem 106 of the device 60, and that the stem 270 slides through a passage 272 formed by an axially-aligned first guide 274 and a second guide 276. In particular, the first guide 274 is located within, and extends slightly in a proximal direction from, the proximal end of the cartridge 62. A flange 278 is formed at the proximal end of the first guide 274, and is in engagement with the finger-rest flange 72 of the cartridge 62. The second guide 276 is located within an opening 280 formed in a proximal end of the first guide 274, where the distal end of the second guide does not seat fully within the opening 280 to provide a gap 282 between interfacing portions thereof. The second guide 276 is also formed with a flange 283 having a proximal end, which seats fully within the opening 280, and which is flush with the proximal end of the flange 278 of the first guide. The flush proximal ends of the first guide 274 and the second guide 276 form a stop surface for a finger rest 285 of the stem 270.

A split, metal O-ring 284, as clearly shown in FIG. 20, is located within the gap 282 and is formed with a separation or split 286 therethrough. A continuous inward surface 288 of the O-ring 284 extends into the passage 272 formed by the first guide 274 and the second guide 276 and forms a first tactile structure in the path of a plurality annular grooves 289 formed on the stem 270 as second tactile structures. As the stem 270 is moved in the distal direction, as viewed in FIG. 18, the O-ring 284 expands about the outer surface of the stem until one of the plurality of grooves 289 moves into the plane of the O-ring, whereby the O-ring contracts. The contraction of the O-ring 284 into one of the grooves 289 provides a tactile indication to the patient-user that one dose of the multiple dose device 268 has been delivered. An O-ring composed of a non-metallic compliant material, without a split, could be used in place of the split, metal O-ring 284 without departing from the spirit and scope of the invention.

Referring to FIGS. 21, 22, 23 and 24, a fourth embodiment of a focused dosimetry device, identified as device 290, is similar to the device 232 as shown in FIGS. 13, 14 and 15, and is typically used in multiple dose applications. Some of the differences reside in the structural relationship between a first guide 292 and a second guide 294, which are in an arrangement similar to the arrangement of the first guide 274 and the second guide 276 of the device 268 (FIGS. 18, 19 and 20). The first guide 292 is assembled in, and with, the proximal end of the carrier 234 essentially in the same manner as the assembly of the guide 246 (FIG. 14) with the carrier. The second guide 294 is assembled with, and partially in an opening 296 of, the first guide 292, with the outer surfaces of the carrier 234, the first guide and the second guide being flush.

A stem 298 of the device 290 is nearly solid, and includes the stem structure 114 with the shoulder 260, as shown in FIG. 14, a thumb piece 300 with thumb rest 302, and a plurality of spaced annular grooves 304 on the outer surface thereof. The O-ring 284 is located between the first guide 292 and the second guide 294, and forms a first tactile structure, while the plurality of spaced annular grooves 304 form a second tactile structure.

Figure 22:
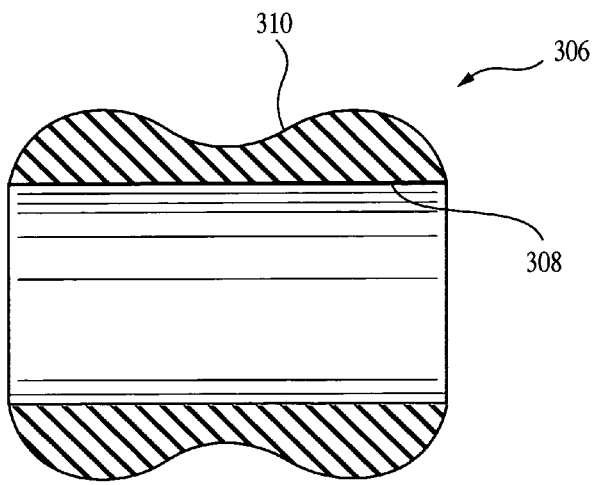
FIG. 22 is a sectional side view showing the finger rest for optional assembly with the focused dosimetry device of FIG. 21, in accordance with certain principles of the invention.
Figure 31:
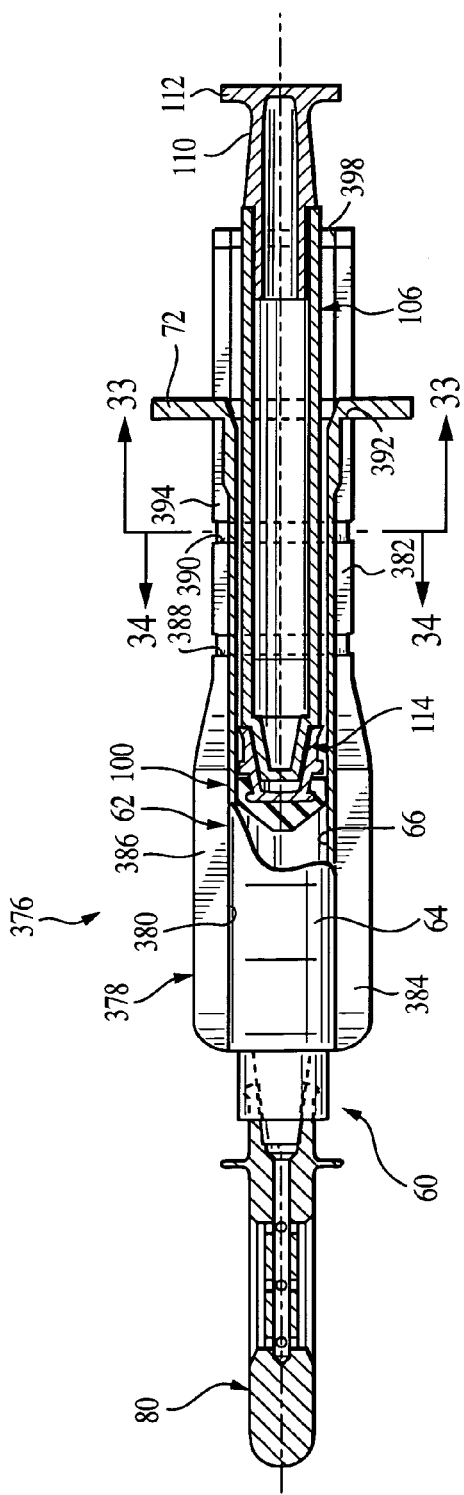
FIG. 31 is a partially-sectioned side view showing a ninth embodiment of a focused dosimetry device, including a cartridge nested in a carrier having spaced slots for receiving a flange of the cartridge, in accordance with certain principles of the invention.

A finger rest 306, as shown in FIG. 22, is formed with an axial passage 308 and an undulating outer surface with a central concave surface 310 for finger placement during administration of the cream. The finger rest 306 is assembled with the device 290 by moving the proximal end of the device through the passage 308 until the proximal end of the finger rest is flush with the proximal end of the second guide 294. In this position, the finger rest 306 covers the outer flush surfaces of the first guide 292, the second guide 294 and a proximal portion of the carrier 234.

The device 290 is used in the same manner as described above with respect to the device 232, as illustrated in FIGS. 13, 14, 15 and 16, with the components thereof being stored in a case in the same manner as the storage of components in the case 266 (FIG. 17).

Referring to FIGS. 25, 26 and 27, a fifth embodiment of a focused dosimetry device, identified as device 312, which typically is used for multiple dose applications. The device 312 includes features which are identical to some of the features of the device 268. In particular, the plunger head 100, the stem 270, the first guide 274, the second guide 276 and the O-ring 284 are identical. Also, a cartridge 314 of the device 312 includes a proximal portion which is identical to the proximal portion of the cartridge 62 (FIGS. 18 and 19).

The differences between the cartridge 62 and the cartridge 314 reside in a distal portion thereof. In particular, a distal end of the cartridge 314 is formed with a closed, rounded nose 316. Further, a distal portion of a wall of the cartridge 314 is formed with a plurality of axially-aligned holes 320, which are closely spaced from each other, and which communicate with a passage 322 of the cartridge.

A sleeve 324, with a flange 326 at the distal end of the sleeve, is secured on the outer surface of the cartridge 314 on the proximal side of the proximal end of the plurality of holes 320. The flange 326 functions as a tactile indicator when the patient-user inserts the nose 316 and the distal portion of the cartridge 314 into the vaginal or anal opening. With this arrangement, the flange 326 provides tactile indication that the plurality of holes 320 are appropriately aligned with the areas of the patient-user to be treated with the cream.

As shown in FIG. 26, a hollow cap 328 is closed at a distal end thereof, and is open, and formed with a flange 330, at a proximal end thereof. The cap 328 is formed to fit over the nose 316 and the portion of the cartridge 314 which includes the plurality of holes 320 to thereby seal the holes to prevent any leakage of cream located within the passage 322 of the cartridge. The flange 330 of the cap 328 is formed with an open receptor 332, with a side wall 334, for receipt of the distal side and peripheral surface of the flange 326, to thereby retain the cap in the position illustrated in FIG. 27. A case 334 is formed with nests for receipt of the assembly of the cartridge 314 and the cap 328, and the stem 270, in a manner similar to the case 168 (FIG. 12).

Referring to FIG. 28, a sixth embodiment of a focused dosimetry device, identified as device 336, is typically used for a single dose application. The device 336 includes features which are identical to some of the features of the device 312. The differences reside in the a plunger 338, a guide 340 and a stem 342. The plunger 338 is a single-piece component composed of a compliant material, which is mounted within the passage 322 of the cartridge 314. The passage 322 of the cartridge 314 contains a single-dose volume of cream such that the plunger 338 is abutting a distal end of the guide 340. The distal end of the stem 342 is insertable into a passage 344 of the guide 340, and engages and moves the plunger 338 in a distal direction to move the single-dose volume of cream through the uncapped holes 320. The distal end of the stem 342 could be attached to the proximal end of the plunger 338, rather than being insertable in and removable from the passage 344 of the guide 340, without departing from the spirit and scope of the invention.

Referring to FIG. 29 a seventh embodiment of a focused dosimetry device, identified as device 346, is typically used for a single dose application. The device 346 includes a cartridge 348 formed with a passage 350, with the applicator 80 attached to the distal end of the cartridge. A first plunger 352 is mounted freely within the passage 350 of the cartridge 348, and is located at a loaded-cream position, as illustrated in FIG. 29. The loaded cream is located between the distal end of the cartridge 348 and the distal end of the first plunger 352. A hole 354 is formed through a wall of the cartridge 348 on the proximal side of the proximal end of the first plunger 352, when the first plunger is in a position assocciated with the passage 350 being fully loaded with the single dose of cream, as illustrated in FIG. 29.

A second plunger 356 is mounted on a distal end of a stem 358, and is inserted into a proximal end of the passage 350 of the cartridge 348. As the second plunger 356 is moved within the passage 350 in the distal direction, air would tend to be entrapped within the passage 350 between the proximal end of the first plunger 352 and the distal end of the approaching second plunger 356. However, due the location of the hole 354, the supposedly entrapped air escapes through the hole and allows the second plunger 356 to advance unimpeded into engagement with the first plunger 352. Upon continued movement of the stem 358 in the distal direction, the first plunger 352 is moved to the distal end of the cartridge to dispense the single dose of cream from the passage 350.

It is noted that additional holes, similar to the hole 354, could be formed in the wall of the cartridge 348, in a transaxial plane including the hole 354, without departing from the spirit and scope of the invention. The additional holes would provide additional escape paths for any supposedly entrapped air.

Referring to FIG. 30, an eighth embodiment of a focused dosimetry device, identified as device 360, is typically used as for multiple dose applications. The device 360 is similar to the device 346, and differs in the addition of three axially-spaced holes 362, 364 and 366, and three stoppers 368, 370 and 372, respectively. Initially, the stoppers 368, 370 and 372 are placed in the respective holes 362, 364 and 366, and the plunger 352 is placed on the distal side of the hole 354, in a manner similar to the plunger location in device 346 with respect to the hole 354. The cream is deposited within the passage 350 from the distal end of the cartridge 348 to fill the space between the distal end of the cartridge and the distal end of the plunger 352. The stoppers 368, 370 and 372 preclude the escape of any cream from within the cartridge 348.

The second plunger 356 of the stem 358 is introduced into the proximal end of the passage 350 and moved to engagement with the proximal end of the first plunger 352. During movement of the second plunger 356 toward engagement with the first plunger 352, any supposedly entrapped air will escape through the hole 354, as described above with respect to the device 346.

Upon continued movement of the second plunger 356 in the distal direction, the first plunger 352 is moved to dispense the initial single dose, of the multiple doses, and the first plunger is moved to the next-dose delivery position, as represented in phantom in FIG. 30. In the next-dose delivery position, the first plunger 352 is on the distal side of the covered hole 362 in the same manner that the first plunger was on the distal side of the hole 354, preceding the delivery of the initial dose of cream from the cartridge 348.

At this time, the stem 358 can be withdrawn, the applicator 80 can be detached and the distal end of the cartridge 348 can be capped, as described above with respect to the device 60. The disassembled components can be cleaned and stored in a case in a manner similar to the storage of components in the case 168 (FIG. 12).

When it is time for the next single-dose application, the components are reassembled and the device 360 is ready for use. The stopper 368 is removed from the hole 362, and, since there is no cream at this location of the cartridge, there is no concern for leakage of cream through the now-open hole 362. The second plunger 356 is moved into the passage 350, and through the passage to engagement with the first plunger 352 in preparation for the delivery of the next single dose. During the time that the second plunger 356 is being moved in the distal direction, but prior to engagement with the first plunger 352, any supposed air entrapped within the passage 350 will be directed through the hole 354 and the open hole 362. In this manner, the second plunger 356 can be moved unimpeded into engagement with the first plunger 352 for delivery of the second single dose of the cream.

The remaining stoppers 370 and 372 can be removed successively in the manner of removal of the stopper 368, as described above, to facilitate delivery of the remaining single dose applications of the cream. In addition, the stoppers 368, 370 and 372 can each be attached to a common strand 374, to retain the removed stoppers together for single disposal.

Figure 32:
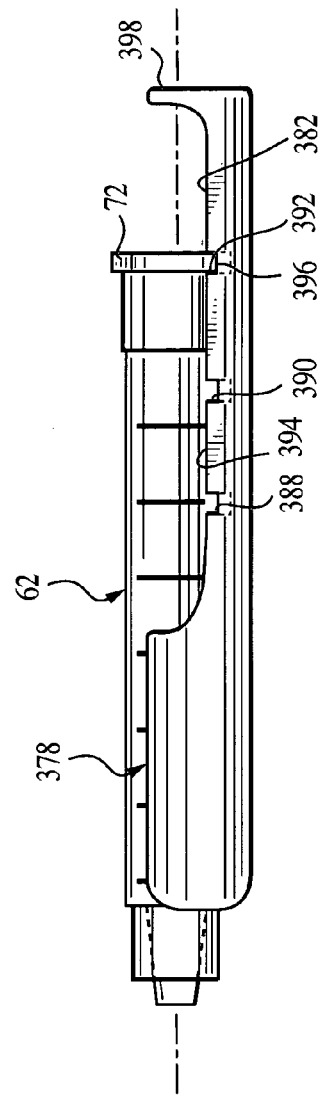
FIG. 32 is a side view showing an assembly of the cartridge and carrier of the focused dosimetry device of FIG. 31, in accordance with certain principles of the invention.
Figure 33:
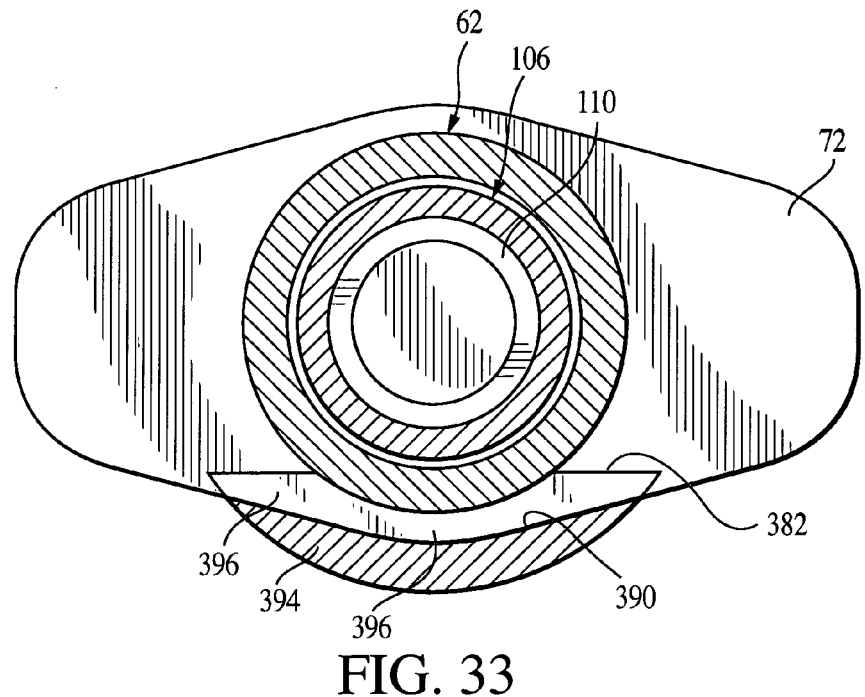
FIG. 33 is a partial section view taken along line 33—33 of FIG. 31 showing the flange of the cartridge of FIG. 31 nested in a respective one of the flange-receiving slots of the carrier, in accordance with certain principles of the invention.
Figure 34:
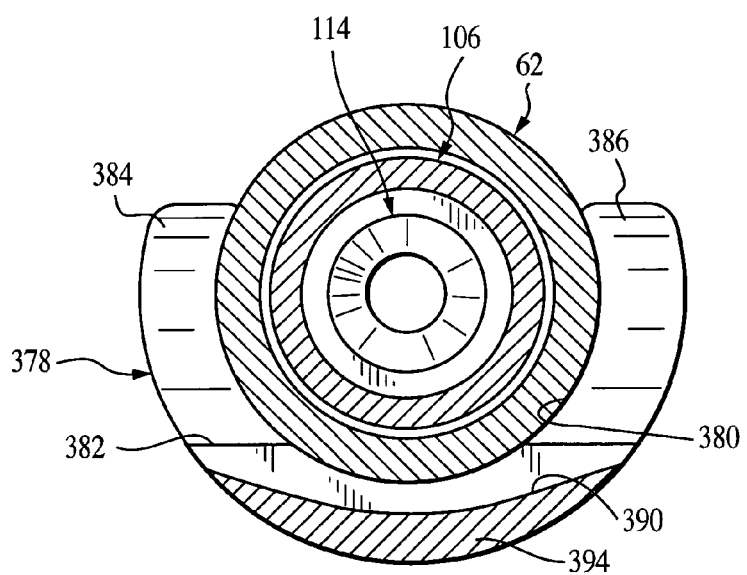
FIG. 34 is a partial section view taken along line 34—34 of FIG. 31 showing the cartridge of FIG. 31 nested in a cartridge-receiving nest of the carrier of FIG. 31, in accordance with certain principles of the invention.

Referring to FIGS. 31, 32, 33 and 34, a ninth embodiment of a focused dosimetry device, identified as device 376, is typically used for multiple dose applications. The device 376 includes the device 60, as shown in FIG. 1. The device 60 includes the cartridge 62, the barrel 64, the passage 66, the finger-rest flange 72, the plunger head 100, the stem 106, the thumb piece 110 and the stem structure 114. The device 376 also includes a carrier 378, which is formed with a C-shaped cartridge-receiving nest 380 and an integrally joined shelf 382. As shown in FIG. 34, the C-shaped nest 380, which is similar to the C-shaped nest 236 of the carrier 234 (FIG. 14), is formed with end portions 384 and 386, which extend above the axis of the cartridge 62 (FIG. 32). This facilitates reception of the cartridge 62 within the nest 380 by a snap fit to retain the cartridge with the carrier 378, in the manner described above with respect to the nest 236 and the cartridge 233.

The shelf 382 extends in a proximal direction from the nest 380, and is fully below the axis of the cartridge 62 as viewed in FIG. 32. Three grooves 388, 390 and 392 are formed transaxially in a portion 394 of the shelf 382, and are formed with a width which will receive a section 396 of the finger-rest flange 72 as shown in FIG. 33. A U-shaped stem guide and stop 398 is formed integrally with the shelf 382 at the proximal end thereof.

In use, the applicator 80 is attached to the distal end of the cartridge 62, and the stem 106 is assembled within the passage 66 of the cartridge, with the stem structure 114 being within the receptor opening 148 of the plunger head 100. The flange 72 is aligned with the groove 388, which is the groove closest to the distal end of the shelf 382, and the cartridge 62 is snapped into the C-shaped nest 380, whereby the flange is moved into the groove. With the stem 106 being in the fully extracted position, the thumb piece 110 extends in the proximal direction from the proximal end of the stop 398, with the extended distance of the thumb piece being representative of a prescribed distance that the stem is to be moved for the delivery of one dose of the cream through the applicator 80.

The patient-user inserts the applicator 80 into the vaginal or anal opening, and applies a force to the thumb piece 110 in the distal direction to move the stem 106 until the thumb rest 112 engages the stop 398. At this time, the plunger head 100 has been moved to a position within the cartridge 62 which is the "start" position for the plunger head for delivery of the next single dose of cream. The components of the device may be disassembled, cleaned, the distal end of the cartridge 62 capped, stored or placed in a case, all in the manner described above.

When the time arrives for delivery of the next dose of the cream, the patient-user reassembles the applicator 80 and the stem 106 with the cartridge 62, and aligns the flange 72 of the cartridge with the middle groove 390 of the carrier 378. The cartridge 62 is then snapped within the nest 380 of the carrier 378, whereby the section 396 of the finger-rest flange 72 is moved into the middle groove 390. At this time, the thumb piece 110 is again extended in the proximal direction from the proximal end of the stop 398 by virtue of having moved the flange 72 to the middle groove 390. A force is applied to the thumb rest 112 to move the stem 106 for the prescribed distance into engagement with the stop 398, which is representative of the delivery of a single dose of the cream through the applicator 80. Again, the components of the device 376 can be disassembled as noted above.

When the time arrives for the application of the third single dose of the cream, the components of the device 376 are reassembled. The section 396 of the flange 72 is aligned with the groove 392, which is the groove closest to the proximal end of the shelf 382, and the cartridge 62 is snapped into the nest 380, whereby the section 396 seats in the groove 392. Again, the thumb piece 110 extends in a proximal direction from the proximal end of the stop 398 by the prescribed distance. A force is applied to the thumb rest 112 and the plunger head 100 is moved to dispense a single dose of the cream through the applicator 80.

The device 376, as described above, includes the three grooves 388, 390 and 392, but could have more or less grooves without departing from the spirit and scope of the invention.

Referring to FIGS. 35, 36, 38, 39 and 40, a tenth embodiment of a focused dosimetry device, identified as device 400, is typically used for multiple dose applications. The device 376 includes the cartridge 62 and the applicator 80. A plunger head 402 includes the plunger 102 and a receptor section 404, which is similar to the receptor section 104, but is formed with a receptor opening 406 having an axially-aligned side wall 408, rather than the tapered side wall at the taper angle "a" in the receptor opening 148. The cross section of the receptor opening 406 could be round, square or any suitable configuration to accomplish the function of the opening.

Figure 39:
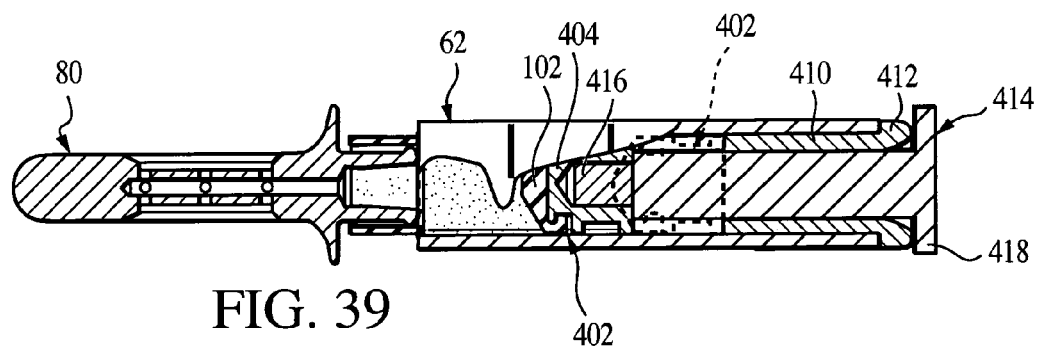
FIG. 39 is a partial section view of the focused dosimetry device of the type shown in FIGS. 35 and 38, showing a first stem of a prescribed length having moved the plunger head to an intermediate location, in accordance with certain principles of the invention.
Figure 40:
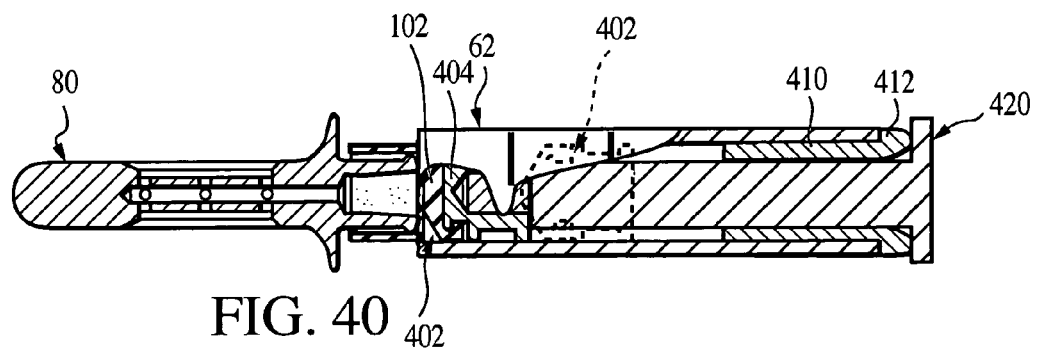
FIG. 40 is a partial section view of the focused dosimetry device of the type shown in FIGS. 35, 38 and 39 showing a second stem of a length greater than the prescribed length having moved the plunger head to an final location, in accordance with certain principles of the invention.
Figure 41:
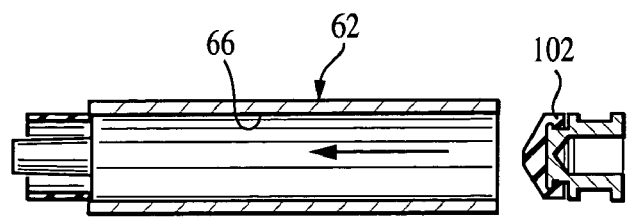
FIG. 41 is a section view of a separated barrel of a cartridge and plunger head.
Figure 42:
FIG. 42 is a section view showing the cartridge barrel of FIG. 41, with the plunger head assembled within, and located at a distal end of, the barrel, in accordance with certain principles of the invention.

A guide 410 is assembled within the proximal end of the passage 66 of the cartridge 62, and is formed with a flange 412, which abuts the proximal end of the cartridge. As shown in FIGS. 35, 36 and 39, a first stem 414 is formed with a prescribed length. Also, the first stem 414 is formed at the distal end thereof with a stem structure 416 which is complementary to the receptor opening 406 for insertion of the stem structure within the receptor opening. The stem 414 is formed with a thumb-rest flange 418 at the proximal end thereof. As shown in FIGS. 36 and 40, the device 400 includes a second stem 420, which is formed in the configuration of the first stem 414, except that the length of the second stem is greater than the prescribed length of the first stem.

Figure 38:
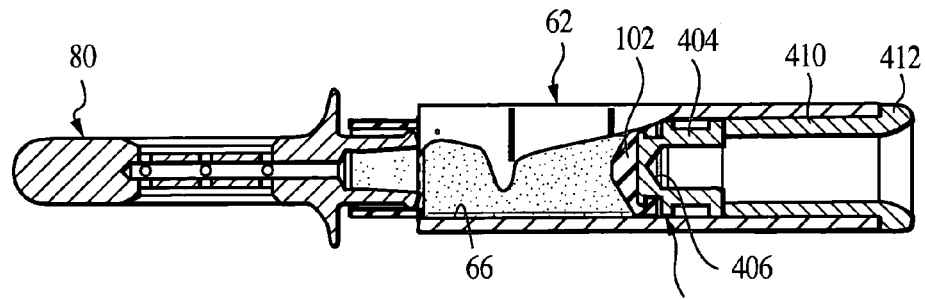
FIG. 38 is a partial section view of a focused dosimetry device of the type shown in FIG. 35, showing an initial volume of a substance within a portion of a cartridge and a plunger head positioned at a prescribed location, in accordance with certain principles of the invention.

In use of the device 400, as shown in FIG. 38, two doses of the cream are placed in the passage 66 of the cartridge 62 and the plunger head 402 is firm against the distal end of the guide 410 to insure proper location of the plunger head for a two-dose application. As shown in FIG. 39, the first stem 414 is moved through the guide 410 so that the stem structure 416 is located within the receptor opening 406 when the plunger head 402 is in a "start" position, as shown in FIG. 38. The "start" position of the plunger head 402 is also shown in phantom in FIG. 39.

The applicator 80 is placed in the vaginal opening or the anal opening, and a force is applied to the thumb-rest flange 418 to move the plunger head 402 in the distal direction. Eventually, the flange 418 engages the proximal end of the guide 410, whereby the plunger head 402, as shown in solid in FIG. 39, has moved a distance sufficient for the dispensing of one dose of the cream through the applicator 80. The components of the device 400 are disassembled, in the manner of disassembly of the components of the above-described devices, and can be cleaned, stored and placed in a case 422, as shown in FIG. 36.

When the time arrives for administering the second of the two doses of cream, the components are reassembled, except that, for the second application, the second stem 420 is used instead of the first stem 414. With the longer second stem 420, as shown in FIG. 40, the plunger head 402 is moved from the position illustrated in phantom to the position illustrated in solid, whereby the second dose of cream is dispensed through the applicator 80.

As shown in FIG. 37, a second embodiment of a cap 424 includes an inner sleeve 426, which extends from a common distal end portion 428, and which is formed with a tapered axial opening 430 and a pair of diametrically-opposed ears 432. This portion of the structure of the cap 424 is similar to the structure at the proximal end of the applicator 80 to fit over the small-diameter tapered sleeve 74 of the cartridge 62, and to threadedly engage the threaded inner wall of the large-diameter sleeve 78. A larger cylindrical outer sleeve 434 extends from the distal end portion 428, and is coaxially located about the inner sleeve 426. When the cap 424 is attached to the distal end of the cartridge 62, the inner sleeve 426 attaches in the same manner as the applicator 80 attaches, and the outer sleeve 434 of the cap surrounds the large-diameter sleeve 78 of the cartridge.

Referring to FIGS. 38, 39 and 40, in a first method of dispensing a substance, such as the cream, from within the cartridge 62, the plunger 102 is located within the axial passage 66 of the cartridge at a prescribed distance from a distal end of the cartridge. Also, an initial volume of the substance is located in a portion of the passage 66 between a distal end of the plunger 102 and a distal end of the cartridge. The method includes the steps of (1) providing the first stem 414 having a first prescribed length which is insertable into the cartridge 62 and which is less than the prescribed distance, (2) placing a distal end of the first stem into the passage 66 from a proximal end of the cartridge and into engagement with a proximal end of the plunger, (3) moving the first stem toward the distal end of the cartridge for a distance less than the prescribed distance, whereby the plunger is moved within the passage toward the distal end of the cartridge to facilitate dispensing from the distal end of the cartridge less than all of the initial volume of the substance, (4) removing the first stem completely from within the passage of the cartridge, (5) providing the second stem 420 having a second prescribed length greater than the first prescribed length, which is insertable into the cartridge, (6) placing a distal end of the second stem into the passage from the proximal end of the cartridge and into engagement with the proximal end of the plunger, and (7) moving the second stem toward the distal end of the cartridge, whereby the plunger is moved within the passage toward the distal end of the cartridge to facilitate dispensing from the distal end of the cartridge an additional amount of the initial volume of the substance.

A second method, which continues from the first method described above, which includes the first stem 414 and the second stem 420, further includes the steps of (1) initially providing the cartridge 62 having the axial passage 66, (2) inserting the plunger 102 into the passage from the proximal end of the cartridge, (3) locating the plunger within the axial passage of the cartridge at the prescribed distance from the distal end of the cartridge, (4) and depositing the initial volume of the substance into the portion of the passage between the distal end of the plunger and the distal end of the cartridge.

A third method, which continues from the first method described above, which includes the first stem 414 and the second stem 420, further includes the steps of (1) initially providing the cartridge 62 having the axial passage 66, (2) inserting the plunger 102 into the passage from the proximal end of the cartridge, (3) locating the plunger at the distal end of the cartridge within the passage, (4) depositing the initial volume of the substance into the passage through the distal end of the cartridge; and (5) moving the plunger toward the proximal end of the cartridge by a force of the initial volume of the substance being deposited into the passage.

Referring to FIGS. 41, 42, 43, 44 and 45, a first method of loading an initial volume of a substance into the cartridge 62 includes the steps of (1) initially providing the cartridge having an axial passage 66, (2) inserting the plunger 102 into the passage from a proximal end of the cartridge, (3) locating the plunger at a distal end of the cartridge within the passage, (4) depositing the initial volume of the substance into the passage through an opening at the distal end of the cartridge; and (5) moving the plunger toward the proximal end of the cartridge by a force of the initial volume of the substance being deposited into the passage.

A second method, which continues from the first method described above, of loading an initial volume of a substance into the cartridge 62, further includes the step of (1) placing the cap 122 over the opening at the distal end of the cartridge.

A third method, which continues from the first method described above, of loading an initial volume of a substance into the cartridge 62, further includes the steps of (1) coupling the applicator 80 over the opening at the distal end of the cartridge, (2) inserting a distal end of the a stem 436 into the passage at the proximal end and into engagement with a proximal end of the plunger 102, and (3) moving the stem, and thereby the plunger, toward the distal end of the cartridge to urge at least some of the substance from the passage, through and from the applicator.

A fourth method, which continues from the first method described above, of loading an initial volume of a substance into the cartridge 62, further includes the step of providing a stop surface 438 (FIGS. 46 and 47) within the passage 66 of the cartridge at a location at which the plunger 102 is to be located when the initial volume of the substance has been deposited in the passage, where, upon depositing the substance into the passage, the force of the initial volume of the substance moves a proximal end of the plunger into engagement with the stop surface to preclude further depositing of the substance into the passage.

It is noted that, while the above-described various embodiments of the devices have included the applicator 80, the applicator 80*a* or the applicator 80*b* could be used with any of the embodiments of the devices which include this type of applicator.

Figure 43:
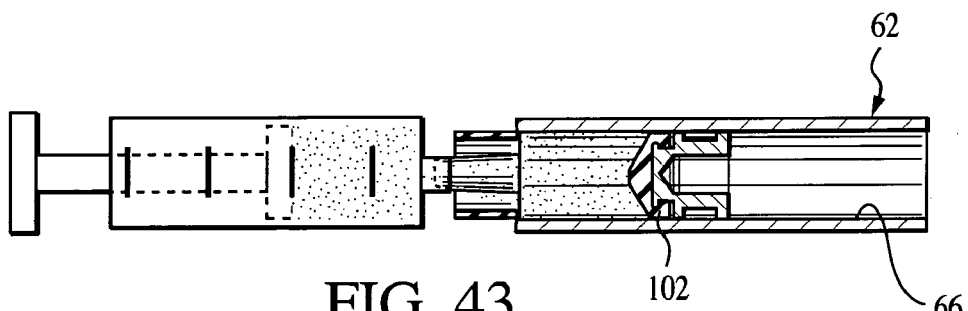
FIG. 43 is a partial section view showing a substance loading device in assembly with the distal end of the cartridge barrel of FIG. 41 with the plunger head being urged away from the distal end of the barrel by the substance being deposited into the barrel, in accordance with certain principles of the invention.
Figure 44:
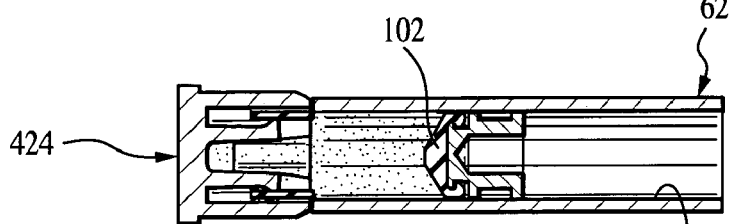
FIG. 44 is a section view showing a substance-loaded cartridge barrel with a cap on the distal end thereof, in accordance with certain principles of the invention.
Figure 45:
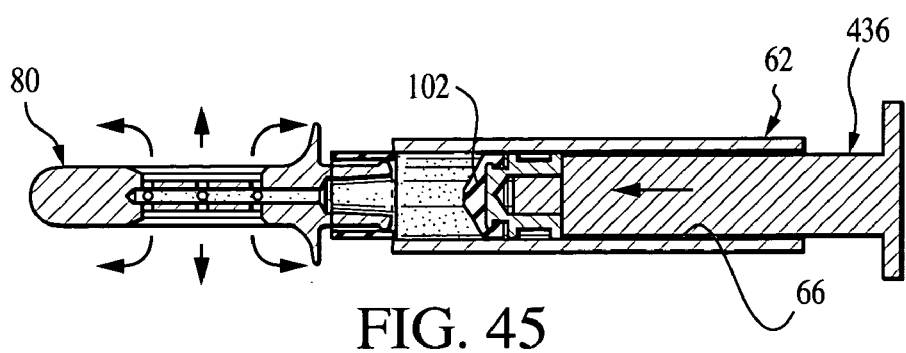
FIG. 45 is a section view showing an applicator assembled on the distal end of the cartridge barrel and a stem moving the plunger head to dispense the substance from within the barrel.
Figure 46:
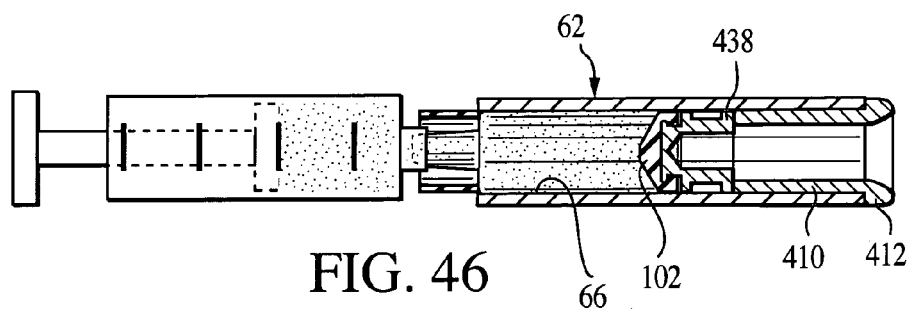
FIG. 46 is a section view showing a substance loading device having loaded the substance into the cartridge barrel and urging the plunger head into a stop surface formed by the distal end of a guide mounted in the proximal end of the cartridge barrel.
Figure 47:
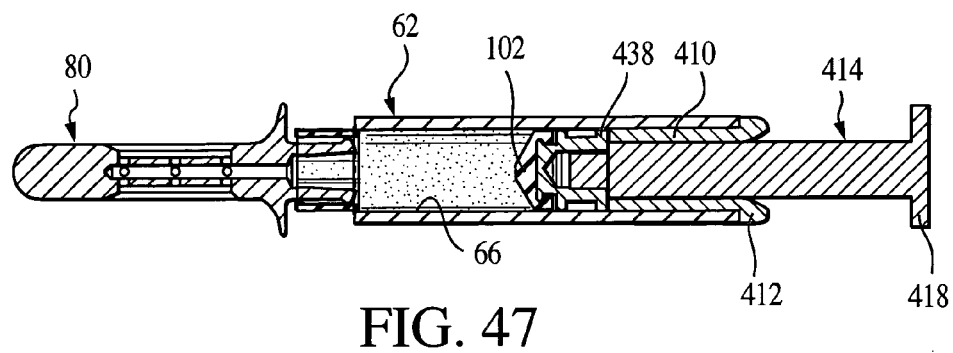
FIG. 47 is a section view of an applicator in assembly with the distal end of the cartridge barrel, and with a stem in position to move the plunger head to dispense the barrel-contained substance into and through the applicator.

It is further noted that, as shown in FIGS. 43 and 46, a substance-supply dispenser 440 is used to transfer the substance from the dispenser to the cartridge 62.

Figure 48:
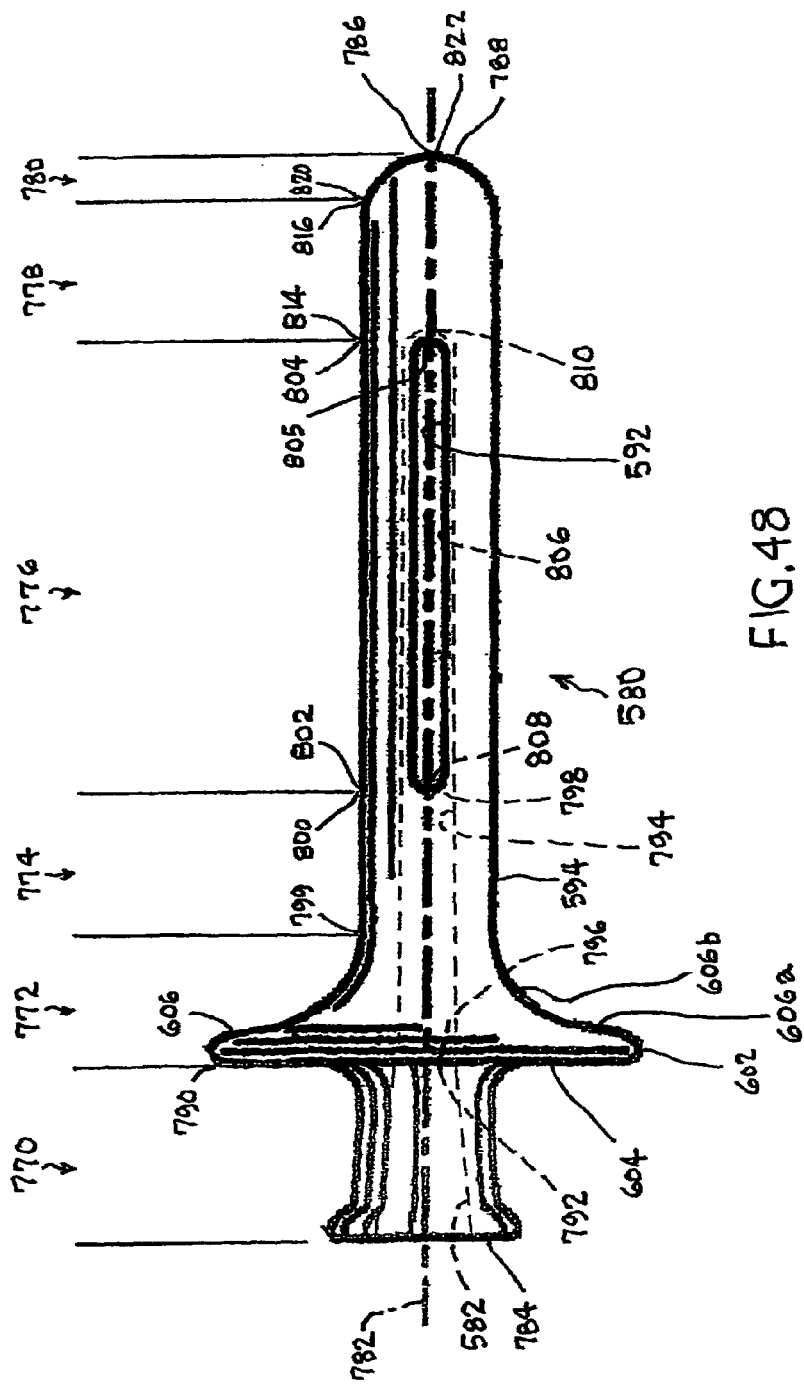
FIG. 48 is a section view of an applicator showing serially-arranged, integrally-joined sections of the applicator extending from a proximal end to a closed distal end thereof in accordance with certain principles of the invention.

Referring to FIG. 48, and in an alternative manner of describing the applicators 80, 80*a* and 80*b*, which are shown in FIGS. 1 through 6, an applicator 580 includes a unitary body 581, formed by six integrally-joined sections, identified as a proximal section 770, a flange section 772, a passage section 774, a slot section 776, a solid section 778, and a dome section 780. As noted above, the applicators 80, 80*a* and 80*b*, as well as the applicator 580, are designed to facilitate the dispensing of a medicinal substance therethrough, where the medicinal substance has a cream-like consistency of the type which does not flow without a force being applied thereto.

The body 581 of the applicator 580 is formed about an axis 782, which extends from a proximal end 784 of the body to an exterior axial surface 786 of a closed distal end 788 of the body. The proximal section 770 of the body 581 extends from the proximal end 784 of the body toward the closed distal end 788 of the body, and to a distal end 790 of the proximal section.

The proximal section 770 of the body 581 is formed with an axial entry passage 582, which extends from the proximal end 784 of the body toward the closed distal end 788 of the body, and to a distal end 792 of the axial entry passage. The axial entry passage 582 is formed with a prescribed diameter, at least at the proximal end 784 of the body.

The body 581 is also formed with an axial intermediate passage 794 having a proximal end 796, which is coincidental with the distal end 792 of the axial entry passage 582. The axial intermediate passage 794 is formed with a uniform passage diameter, which is less than the prescribed diameter, and extends toward the closed distal end 788 of the body 581, and to a distal end 798 of the axial intermediate passage.

The body 581 is formed about the axis 782 thereof with the passage section 774, which has a uniform exterior diameter. The passage section 774 extends from a proximal end 799 thereof toward the closed distal end 788 of the body, and to a distal end 800 of the passage section, and fully surrounds at least a portion of the axial intermediate passage 794 to the distal end 798 thereof.

The body 581 is formed about the axis 782 thereof with the slot section 776, which has the uniform exterior diameter. The slot section 776 extends from a proximal end 802 thereof toward the closed distal end 788 of the body 581, and to a distal end 804 of the slot section, with the proximal end 802 of the slot section formed integrally with the distal end 800 of the passage section 774.

A slot delivery passage 806 is formed axially through the slot section 776 of the body 581 from a proximal end 808 of the slot delivery passage toward the closed distal end 788 of the body, and to a closed distal end 810 of the slot delivery passage, with the proximal end 800 of the slot delivery passage being in communication with the distal end 798 of the axial intermediate passage 794.

At least one axially-elongated slot 592 is formed radially through the slot section 776 of the body 581 in unobstructed radial communication with the slot delivery passage 806 and an exterior of the body, and extends from the proximal end 802 of the slot section toward the distal end 804 thereof, and to a distal end 805 of the at least one axially-elongated slot. The slot delivery passage 806 is formed with the uniform passage diameter, interrupted only by the presence of the at least one axially-elongated slot 592.

The body 581 is formed with the solid section 778, having the uniform exterior diameter, which extends from a closed proximal end 814 of the solid section toward the closed distal end 788 of the body, and to a closed distal end 816 of the solid section. The closed proximal end 814 of the solid section 778 is formed integrally with the distal end 804 of the slot section 776.

The body 581 is formed with the dome section 780 in the form of a solid dome 818, which extends from a closed proximal end 820 of the dome section to a closed distal end 822 thereof, which is coincidental with the exterior axial surface 786 of the closed distal end 788 of the body 581. The closed proximal end 820 of the dome section 780 is formed integrally with the closed distal end 816 of the solid section 778. The solid section 778 and the dome section 780 are exclusive of any opening.

It is noted that the axial intermediate passage 794 of the passage section 774, and the slot delivery passage 806 of the slot section 776, are axially aligned and combine to form the inner passage 90, as illustrated, for example, in FIGS. 5 and 6. Further, as described above, and with reference to FIG. 48, the axially-aligned axial intermediate passage 794 and the slot delivery passage 806 are formed with the uniform passage diameter.

As further shown in FIG. 48, a flange 598 is located in the flange section 772, between the proximal section 770 and the passage section 774. The flange 598 is integrally joined with adjacent portions of the body 581, at opposite axial ends thereof, and fully radially surrounds a portion of the axial intermediate passage 794. Thus, except for the presence of the at least one axially-elongated slot 592, successive portions of the body 581, which are located in the three sections identified as the flange section 772, the passage section 774 and the slot section 776, surround the axial delivery passage 90 (FIG. 5), which, as noted above, is formed by the axial intermediate passage 794 and the slot delivery passage 806 illustrated in FIG. 48.

Referring to FIG. 48, the flange 598 extends radially outward from an exterior surface 594 of the body 581 to an outer edge surface 602 of the flange. The flange 598 is formed with a proximal surface 604 facing in a direction toward the proximal end 784 of the body 581 and a distal surface 606 facing in a direction toward the closed distal end 788 of the body. The distal surface 606 of the flange 598 is formed by a straight portion 606a which extends from the outer edge surface 602 of the flange, radially inward toward the axis 782 of the body 581 and toward the closed distal end 788 of the body, to an inboard edge of the straight portion spaced radially outward from the external surface of the body. The distal surface 606 of the flange 598 is further formed with a concave portion 606b which extends from the inboard edge of the straight portion 606a toward the closed distal end 788 of the body 581, and to the external surface 594 of the body.

Thus, with the structure of the body 581 as described above, there is full communication from an exterior of the body 581, at the proximal end 784 thereof, through the axial entry passage 582, the axial intermediate passage 794, the slot delivery passage 806, the at least one axially-elongated slot 592, and an exterior of the body adjacent the at least one axially-elongated slot.

In general, the above-identified embodiments are not to be construed as limiting the breadth of the present invention. Modifications, and other alternative constructions, will be apparent which are within the spirit and scope of the invention as defined in the appended claims.

What is claimed is:

1. A method of applying a medicinal substance directly onto an area to be treated within a body cavity of a patient, where the substance has a cream-like consistency of the type which does not flow easily without a force being applied thereto, which comprises the steps of:

providing an applicator having a body formed about an axis which extends from a proximal end of the body to an exterior axial surface of a closed distal end of the body; the body formed with a proximal section which extends from the proximal end of the body toward the closed distal end of the body, and to a distal end of the proximal section; the proximal section of the body formed with an axial entry passage extending through the proximal section from the proximal end of the body toward the closed distal end of the body, and to a distal end of the axial entry passage; the axial entry passage being formed with a prescribed diameter at the proximal end of the body; the body being formed with an axial intermediate passage having a proximal end in communication with the distal end of the axial entry passage, and extending toward the closed distal end of the body, and to a distal end of the axial intermediate passage; the axial intermediate passage being formed with a uniform passage diameter which is less than the prescribed diameter; the body being formed about the axis thereof with a passage section, having a uniform exterior diameter, which extends from a proximal end thereof toward the closed distal end of the body, and to a distal end of the passage section; the body is further formed with a flange section which extends from a proximal end of the flange section toward the closed distal end of the body, and to a distal end of the flange section; the body formed with a flange section having a proximal end formed integrally with the distal end of the proximal section, and a distal end formed integrally with the proximal end of the passage section of the body; a flange located in the flange section of the body and extending radially outward from the external surface of the body to an outer edge surface of the flange; the passage section of the body fully surrounding at least a portion of the axial intermediate passage to the distal end of the axial intermediate passage; the body being formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section; a slot delivery passage formed axially through the slot section of the body from a proximal end thereof toward the closed distal end of the body, and to a closed distal end of the slot delivery passage, with the proximal end of the slot delivery passage being in communication with the distal end of the axial intermediate passage; at least one axially-elongated slot formed radially through the slot section of the body in unobstructed communication with the slot delivery passage and an exterior of the body, and extending from the proximal end of the slot section toward the distal end of the slot section, and to a distal end of each the at least one axially-elongated slot; the slot delivery passage being formed with the uniform passage diameter interrupted only by the presence of the at least one axially-elongated slot; the body formed with a solid section, having the uniform exterior diameter, which extends from a closed proximal end of the solid section toward the closed distal end of the body, and to a closed distal end of the solid section, with the closed proximal end of the solid section being formed integrally with the distal end of the slot section; the body formed with a dome section in the form of a solid dome, which extends from a closed proximal end of the coincidental with the exterior axial surface of the closed distal end of the body; the closed proximal end of the dome section being formed integrally with the closed distal end of the solid section; and the solid section and the dome section being exclusive of any opening;

locating the slot delivery passage adjacent the area of the body cavity to be treated;

forming a mass of the substance externally of the body cavity;

moving the mass of the substance into the slot delivery passage such that the mass of the substance extends between a location adjacent the area to be treated and a location adjacent a portion of the body cavity opposite the area to be treated; and moving at least a portion of the mass of the substance from the slot delivery passage, transaxially through the at least one axially-elongated slot, and directly onto the area to be treated within the body cavity.

2. The method as set forth in claim 1, where, in the step of providing an applicator, the flange having a proximal surface facing in a direction toward the proximal end of the body and a distal surface facing in a direction toward the closed distal end of the body; the distal surface of the flange formed by a straight portion which extends from the outer edge of the flange, radially inward toward the axis of the body and toward the closed distal end of the body, to an inboard edge of the straight portion spaced radially outward from the external surface of the body; and the distal surface of the flange formed with a concave portion which extends from the inboard edge of the straight portion toward the distal end, and to the external surface, of the body.

3. The method as set forth in claim 1, where, in the step of providing the applicator, the slot section of the body is formed with an axial length which is greater than an axial length of the solid section of the body.

* * * * *